US007785819B2

(12) United States Patent
Robinson et al.

(10) Patent No.: US 7,785,819 B2
(45) Date of Patent: Aug. 31, 2010

(54) THERAPEUTIC AND DIAGNOSTIC USES OF ANTIBODY SPECIFICITY PROFILES

(75) Inventors: William H. Robinson, Menlo Park, CA (US); David L. Hirschberg, Menlo Park, CA (US); Lawrence Steinman, Palo Alto, CA (US); Pedro Jose Ruiz, Redwood City, CA (US); Paul J. Utz, Stanford, CA (US); Hideki Garren, Stanford, CA (US)

(73) Assignee: The Board of Trustees of the Leland Stanford Junior University, Palo Alto, CO (US)

( * ) Notice: Subject to any disclaimer, the term of this patent is extended or adjusted under 35 U.S.C. 154(b) by 1284 days.

(21) Appl. No.: 10/120,578

(22) Filed: Apr. 10, 2002

(65) Prior Publication Data

US 2003/0003516 A1    Jan. 2, 2003

Related U.S. Application Data

(60) Provisional application No. 60/283,090, filed on Apr. 10, 2001.

(51) Int. Cl.
*G01N 33/00* (2006.01)
(52) U.S. Cl. .................................................. 435/7.92
(58) Field of Classification Search .................. 435/7.9, 435/4, 6, 7.1, 7.2, 7.21, 7.8, 7.91–7.95, 973, 435/287.1, 287.2; 436/514, 518
See application file for complete search history.

(56) References Cited

U.S. PATENT DOCUMENTS

| | | | |
|---|---|---|---|
| 4,136,160 A * | 1/1979 | Cohen | 424/1.57 |
| 4,865,970 A | 9/1989 | Brot et al. | |
| 5,270,167 A * | 12/1993 | Francoeur | 435/7.21 |
| 5,354,691 A | 10/1994 | Van Eden et al. | |
| 5,486,452 A * | 1/1996 | Gordon et al. | 435/5 |
| 5,578,496 A | 11/1996 | Atassi et al. | |
| 5,637,454 A | 6/1997 | Harley | |
| 5,656,272 A * | 8/1997 | Le et al. | 424/133.1 |
| 5,747,035 A * | 5/1998 | Presta et al. | 424/144.1 |
| 5,750,356 A * | 5/1998 | Spack et al. | 435/7.24 |
| 5,763,158 A | 6/1998 | Bohannon | |
| 6,022,697 A | 2/2000 | Kaufman et al. | |
| 6,183,988 B1 * | 2/2001 | Bloch et al. | 435/69.1 |
| 6,207,645 B1 | 3/2001 | Howell et al. | |
| 6,232,088 B1 | 5/2001 | Franklin et al. | |
| 6,241,985 B1 | 6/2001 | Madiyalakan et al. | |
| 6,252,040 B1 * | 6/2001 | Warren et al. | 530/328 |
| 6,287,874 B1 * | 9/2001 | Hefti | 436/501 |
| 6,544,523 B1 * | 4/2003 | Chu | 424/192.1 |
| 6,995,237 B1 * | 2/2006 | Zimmerman | 530/324 |
| 7,201,896 B1 * | 4/2007 | Revel et al. | 424/85.2 |

FOREIGN PATENT DOCUMENTS

| | | |
|---|---|---|
| EP | 0 063 810 A1 | 11/1982 |
| EP | 0 569 800 A1 | 11/1993 |
| EP | 0940470 A2 | 9/1999 |
| JP | 6-34629 T | 2/1994 |
| JP | 6-504114 T | 5/1994 |
| JP | 7-509221 T | 10/1995 |
| WO | WO 91/11718 A1 | 8/1991 |
| WO | WO 93/21223 A1 | 10/1993 |
| WO | WO 99/39210 | 8/1999 |
| WO | WO 00/39580 | 7/2000 |

OTHER PUBLICATIONS

Joos et al., "A microarray enzyme-linked immunosorbent assay for autoimmune diagnostics", Weinheim, 2000, pp. 2641-2650.*
(http://www.m-w.com/cgi-bin/dictionary?book=Dictionary &va=antigen, Jun. 24, 2007, Merriam-Webster's, On-line Dictionary, 10th edition.*
Staykova et al., ["Infusion of soluble myelin basic protein protects long term against induction of experimental autoimmune encephalomyelitis" Immunology and Cell Biology (1997) 75, 54-64].*
Altman et al., Phenotypic Analysis of Antigen-Specific T Lymphocytes, (1996), Science, 274 (5284): 94-6.
Bielekova et al., Encephalitogenic Potential of the Myelin Basic Protein Peptide (Amino Acids 83-99) in Multiple Sclerosis: Results of a Phase II Clinical Trial With an Altered Peptide Ligand, (2000), Nat. med., 6: 1167-1175.
Critchfield et al., T Cell Deletion in High Antigen Dose Therapy of Autoimmune Encephalomyelitis, (1994), Science, 263: 1139-43.
Garren et al., Combination of Gene Delivery and DNA Vaccination to Protect From and Reverse TH1 Autoimmune Disease Via Deviation to the Th2 Pathway, ( 2001), Immunity, 15(1): 15-22.
Kappos et al., Induction of a Non-Encephalitogenic Type 2 T Helper-Cell Autoimmune Response in Multiple Sclerosis After Administration of an Altered Peptide Ligand in a Placebo-Controlled, Randomized Phase II Trial, (2000), Nature Medicine, 6:1176-1182.

(Continued)

*Primary Examiner*—Ann Y Lam
(74) *Attorney, Agent, or Firm*—Townsend and Townsend and Crew LLP

(57) ABSTRACT

This invention provides a method for determining the antibody specificity profile in an individual. This specificity profile reveals the individual's immune response to multiple antigens and/or epitopes of autoantigens, allergens, graft antigens, etc. The antibody specificity profile is determined through the binding of patient samples comprising antibodies to the arrays. The array can comprises antigens and epitopes. The invention also provides the means and methods for determining antigen or epitope specificity profiles that can be used in the development of either generic and individualized diagnosis and treatment for immune related diseases, including autoimmune disease, allergy and graft rejection.

18 Claims, 6 Drawing Sheets

OTHER PUBLICATIONS

Ruiz et al., Microbial Epitopes Act as Altered Peptide Ligands to Prevent Experimental Autoimmune Encephalomyelitis, (1999), J. Exp. Med., 189: 1275-1283.

Ruiz et al., Suppressive Immunization With DNA Encoding a Self-Peptide Prevents Autoimmune Disease: Modulation of T Cell Costimulation, (1999), J. Immunol., 162: 3336-3341.

Steinman et al., Absence of "Original Antigenic Sin" in Autoimmunity Provides an Unforeseen Platform for Immune Therapy, (1999), J. Exp. Med., 189: 1021-1024.

Touhy et al., Spontaneous Regression of Primary Autoreactivity During Chronic Progression of Experimental Autoimmune Encephalomyelitis and Multiple Sclerosis, (1999), J. Exp. Med., 189: 1033-1042.

Garren, H. et al., "Combination of gene delivery and DNA vaccination to protect from and reverse Th1 autoimmune disease via deviation to the Th2 pathway," *Immunity*, 15:15-22 (Jul. 2001).

Joos, T. et al., "A microarray enzyme-linked immunosorbent assay for autoimmune diagnostics", *Electrophoresis*, 21(13):2641-2650 (2000).

Lobell, A. et al., "Vaccination with DNA encoding an immunodominant myelin basic protein peptide targeted to Fc of immunoglobulin G suppresses experimental autoimmune encephalomyelitis," *J. Exp. Med.*, 187(9):1543-1548 (May 4, 1998).

Piccirillo, C. and Prud'Homme G., "Prevention of experimental allergic encephalomyelitis by intramuscular gene transfer with cytokine-encoding plasmid vectors," *Human Gene Therapy*, 10:1915-1922 (Aug. 10, 1999).

Robinson, W. et al., "Autoantigen microarrays for multiplex characterization of autoantibody responses," *Nature Medicine*, 8(3):295-301 (Mar. 2002).

Robinson, W. et al., Abstract—"Protein array characterization of the specificity of the autoantibody response in experimental autoimmune encephalomyelitis: Examination of the role of epitope spreading in disease progression", *FASEB J.*, 15(5):A1064 (Mar. 8, 2001).

Selmaj, K. et al., "Naked DNA vaccination differentially modulates autoimmune responses in experimental autoimmune encephalomyelitis," *J. Neuroimmun.*, 111:34-44 (Nov. 1, 2000).

Hueber, Wolfgang et al.; "Autoantibody profiling for the study and treatment of autoimmune disease"; 2002, *Arthritis Research*, vol. 4, No. 5, pp. 290-294.

Joos, T., et al., "A microarray enzyme-linked immunosorbent assay for autoimmune diagnostics," *Electrophoresis*, vol. 21, pp. 2641-2650 (2000).

\* cited by examiner

A. Normal Rat Serum

B. Rat EAE induced with MBPp68-86

C. Rat EAE induced with PLPp139-151

D. Rat EAE induced with MOGp35-55

| j. Quantitative Analysis | | | | | | | | | |
|---|---|---|---|---|---|---|---|---|---|
| Ag Feature | Norm | Sjögren | SLE | PM | MCTD | PBC | Sclero-D | Sclero-L | RA |
| DNA | 78 | 352 | 16,905 | 0 | 5,001 | 1 | 314 | 37 | 26 |
| Histone II-A | 93 | 44 | 3,009 | 0 | 918 | 1 | 100 | 60 | 0 |
| Ro52 | 374 | 20,934 | 196 | 17,396 | 1,818 | 93 | 280 | 121 | 143 |
| La | 108 | 8,102 | 564 | 0 | 0 | 1 | 119 | 6 | 0 |
| U1-70kDa | 190 | 135 | 6,825 | 31 | 2,315 | 159 | 274 | 77 | 153 |
| SR protein | 262 | 629 | 8,745 | 112 | 135 | 342 | 237 | 182 | 0 |
| hnRNP B1 | 379 | 269 | 1,416 | 428 | 978 | 381 | 458 | 317 | 713 |
| CENP B | 12 | 33 | 435 | 21 | 0 | 262 | 11 | 11,947 | 0 |
| Topo I | 91 | 113 | 551 | 0 | 11 | 1 | 10,095 | 27 | 0 |
| Jo-1 | 24 | 97 | 334 | 28,753 | 0 | 1 | 485 | 0 | 3 |
| PDH | 190 | 40 | 377 | 40 | 75 | 6,609 | 222 | 526 | 279 |
| Influenza | 15,065 | 19,809 | 13,521 | 1,266 | 18,686 | 1 | 11,641 | 475 | 9,134 |
| Pneumoc | 15,580 | 8,153 | 29,669 | 2,779 | 30,473 | 1 | 20,509 | 5,729 | 18,374 |
| MBP 68-86 | 99 | 13 | 314 | 8 | 0 | 7 | 46 | 40 | 0 |

Antigen array analysis of the specificity of the autoantibody response in cerebral spinal fluid from control and multiple sclerosis patients.

A. SJL Mouse - normal control    B. SJL EAE Mouse-1    C. SJL EAE Mouse-2

Antigen array characterization of the specificity of the autoantibody response in mice with EAE.

A. Normal control mouse serum        B. Collagen-induced arthritis mouse serum

'Synovial proteome' array analysis of the autoantibody response in the murine CIA model for RA.

Figure 6.

Cluster analysis demonstrates that DNA tolerizing vaccine treatment reduces epitope spreading of the autoantibody response in relapsing EAE.

THERAPEUTIC AND DIAGNOSTIC USES OF ANTIBODY SPECIFICITY PROFILES

BACKGROUND OF THE INVENTION

The astonishing complexity of the immune system is its greatest strength. The $10^{12}$-$10^{14}$ possible antibody specificities, the delicate interplay between the various regulatory and effector cells, the restriction of T cell responses according to MHC antigens; all these contribute to the ability of the host to effectively react against infectious agents and other antigens perceived as foreign. But this diversity has its drawbacks. Mistakes happen: the target of a response may turn out to be a normal self protein; inflammatory responses are misregulated; and normal responses are undesirably directed against grafts and transplanted cells. Under these circumstances, the complexity of the system makes diagnosis and therapy extremely difficult.

For most autoimmune diseases, atopic states and undesired immune responses, no effective diagnostic blood tests or therapeutic agents exist. For example, current therapeutic strategies are often based on system-wide immune suppression. Since this treatment is not antigen specific, the result is a global decrease in immune function, resulting in susceptibility to infection and disease. Therefore, there is a tremendous clinical need for antigen-specific diagnosis and tolerizing therapies, which will specifically turn off undesired immune responses, but will leave the remainder of the immune system intact. However, in order to provide antigen specific therapy, the antigen specificity of reactive cells needs to be defined.

The importance of defining antigenic targets in autoimmune disease is in part related to the progression of these diseases. For example, immune responses in the neurodegenerative diseases such as multiple sclerosis (MS) and experimental autoimmune encephalomyelitis (EAE) may be directed against one or more myelin sheath proteins, for example myelin basic protein, myelin oligodendroglial glycoprotein, proteolipid protein, and various other myelin antigens. As the disease progresses, reactivity to the initiating antigen diminishes, and an orderly and definable set of new immune reactivities arises. Over time, antigen-specific autoimmune responses can spread to different epitopes on one protein, termed "intramolecular epitope spreading", or to other epitopes on other structural proteins, termed "intermolecular epitope spreading". During the course of EAE initiated by immunization to one epitope, both intramolecular and intermolecular epitope spreading allow the autoimmune response to evolve to encompass detectable T cell responses to other epitopes on the initiating antigen and to other myelin antigens (see Steinman (1999) *J. Exp. Med.* 189:1021-1024).

As described by Touhy et al. (1999) *J. Exp. Med.* 189:1033-1042, patients lose reactivity to the myelin epitopes that were recognized during the initial immune response, and develop T cell immune reactivity to other myelin epitopes. The immune response to the initiating self-antigen in autoimmunity can eventually disappear, as the disease enters the stage where clinical progression and then chronicity prevail. However, critical immunogenic epitopes can still be found in chronic disease states, and these provide a key to antigen specific therapy.

Before antigen specific therapies can be provided, a more precise and high throughput method of diagnosis is required, as well as a means of delivering specific immunosuppressive agents. Achieving diagnosis is particularly difficult where there is a strong T cell component to the autoimmune disease, due to the T cell receptor recognition of antigen only when bound to an appropriate major histocompatibility protein.

Although precise identification of the cognate antigen for T cells remains challenging (see Altman et al. (1996) *Science* 274(5284):94-6), techniques exist for serotyping of antibody specificities. Many assays are known and used in the art for detection of antibodies with a particular specificity, including ELISA, RIA, competitive and non-competitive sandwich assays, solid phase immunoassays, e.g. on porous supports (see U.S. Pat. No. 5,486,452), and the like. For example, Atassi et al. (1996) U.S. Pat. No. 5,578,496 define the fine specificity of autoantibodies by solid-phase radioimmunoassay using overlapping peptides derived from a target antigen. Similarly, Harley (1997) U.S. Pat. No. 5,637,454 performed solid phase anti-peptide assays to determine the specificity of autoantibodies against the SSA protein.

Therapies aimed at antigen specific responses are being developed. In some instances, peptides are being delivered to the host in a manner that induces tolerance to the antigen. For example, phase II clinical trials are underway for the treatment of MS with myelin basic protein altered peptides. The results of clinical trials are described in Kappos et al. (2000) *Nature Medicine* 6:1176-1182; and Bielekova et al. (2000) *Nat. Med.* 6:1167-1175 Microbial peptides that act as altered peptide ligands are described by Ruiz et al. (1999) *J. Exp. Med.* 189:1275-1283. Delivery of purified myelin proteins targeted by the autoimmune response have also demonstrated efficacy in treating EAE (Critchfield et al (1994) *Science* 263:1139-43). DNA sequences encoding autoantigens have also been used to promote antigen-specific immunosuppression. Ruiz et al. (1999) *J. Immunol.* 162:3336-3341 vaccinate with a minigene encoding a dominant epitope of myelin proteolipid protein, and demonstrate protection from disease. Garren et al. (2001) vaccinate with a cocktail of minigenes encoding 4 antigens, demonstrating enhanced protection and treatment of active disease.

There is an unmet need for methods of accurately and quickly performing diagnosis of the autoantigen repertoire being recognized by immune cells in clinical disease states, and for the translation of this knowledge into specific therapeutic modalities. The present invention addresses this issue.

SUMMARY OF THE INVENTION

Objects of the present invention are accomplished by a novel method of determining an antibody specificity profile in a patient with an immune-related disease comprising: (a) preparing an antigen array comprising at least two disease associated antigens wherein said antigens further comprise one or more immunologic epitope(s); (b) physically contacting the antigen array from step (a) with a patient sample comprising antibodies; (c) identifying the disease associated antigens within the microarray that bind to antibodies within the patient sample from step (b); (d) comparing the antibodies bound to the disease associated antigens in step (c) with (1) antibodies binding to the disease associated antigens within the microarray of step (a) wherein the antibodies are known to be associated with the disease; and, (2) antibodies binding to the disease associated antigens within the microarray of step (a) wherein the antibodies are not associated with the disease. Objects of the present invention are also accomplished by a novel method of determining an antibody specificity profile in a patient with an immune-related disease comprising: (a) preparing an epitope array comprising one or more disease associated epitope(s); (b) physically contacting the epitope array from step (a) with a patient sample comprising antibodies; (c) identifying the disease associated epitope(s) within the microarray that bind to antibodies within the patient sample from step (b); (d) comparing the antibodies bound to the disease associated epitope(s) in step (c) with (1) antibodies binding to the disease associated epitope(s) within the microarray of step (a) wherein the antibodies are known to be associated with the disease; and, (2) antibodies binding to the disease associated epitope(s) within the microarray of step (a) wherein the antibodies are not associated with the disease. The novel method of determining an antibody specificity profile also provides the ordinarily skilled artisan with an antigen profile or an epitope profile, as the case may be. The methods and compositions of this invention are used for diagnosis and for design and selection of specific therapies for immune-related diseases. More specifically the methods and compositions related to determining an antibody specificity profile can be used for autoimmune disease, including immune related disorders such as multiple sclerosis (MS), rheumatoid arthritis (RA), autoimmune diabetes, systemic lupus erythematosus (SLE), myositis, scleroderma, psoriatic arthritis, primary biliary cirrhosis (PBC), myasthenia gravis (MG), polychondritis, and tissue transplant rejection. Further, the method for determining an antibody specificity profile is used in allergy. In one embodiment, a high throughput determination is made of the spectrum of disease relevant antibodies present in patient serum by detailed binding analyses of these antibodies. The antibody specificity profile reveals the individual's complex immune response directed to one or more antigens having one or more epitopes.

The invention provides a method for determining the antibody specificity profile to identify those patients likely to develop an immune-related disorder, but who have not yet manifested symptoms.

The invention also provides a method for the identification of patients likely to develop a more severe form of disease, enabling selection of more aggressive therapy based on a patient's antibody specificity profile.

The invention also provides a method for the design of treatment regimens, including antigen-specific and non-antigen specific therapies. In one embodiment, antigen-specific therapies are selected based on the antibody-specificity profile. The patient antibody specificity profile provides information about both B cell and T cell mediated responses, Individualized cocktails of antigen specific treatments can be formulated based on the patient's specificity profile. In another embodiment, identification of a consensus of common antibody specificity profiles between patients with the same immune disorder provides for formulation of a generic antigen-specific therapy to treat patients with that disease.

In yet another aspect of the invention, there are methods for determining the antibody specificity profile for monitoring therapeutic response in patient receiving treatment for immune-related disorders. Therapeutic responses are assessed based on alterations in the antibody specificity profile including changes in antibody targets (i.e. the antigen or epitope profile), changes in antibody titers, changes in antibody isotypes, and changes in large-scale patterns of antibody recognition. In another embodiment, antibody specificity profiles can be utilized to predict adverse outcomes in individual patients, thereby enabling selection of alternative therapies.

In another aspect, the antibody specificity profile enables identification of novel antigens associated with the disease and novel epitopes associated with the disease.

Bound antibodies were detected using Cy-3-conjugated goat-anti-human IgM/IgG prior to scanning.

Figure 3:
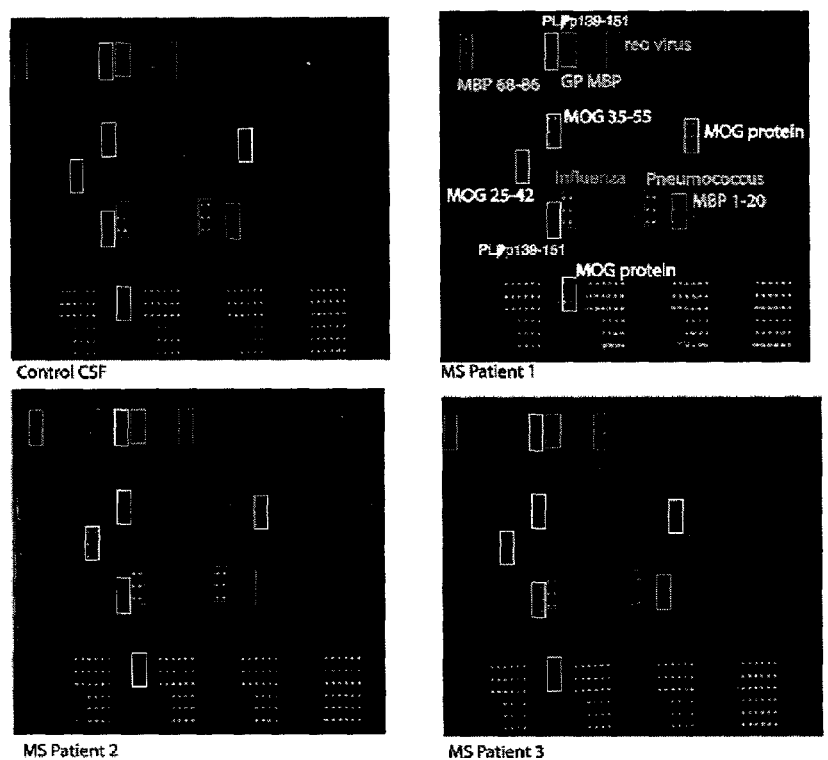

FIG. 3 shows an antibody specificity profile including an antigen array characterization (antigen array profile) of the autoantibody response in cerebral spinal fluid from human multiple sclerosis patients. 2400-spot 'myelin proteome' arrays were produced by spotting putative myelin antigens (described in text) using a robotic microarrayer, probed with cerebral spinal fluid followed by Cy-3-labeled anti-human Ig secondary antibody, scanned using a GenePix scanner, and images analyzed using GenePix software to determine levels of autoantibody binding to each spot. These arrays contain 400 different myelin protein and peptide epitopes including MBP, proteolipid protein (PLP), myelin oligodendrocyte protein (MOG), overlapping peptides representing these proteins, and peptides representing dominant epitopes from additional myelin autoantigens including cyclic nucleotide phosphodiesterase (CNPase), myelin-associated glycoprotein (MAG), and myelin-associated oligodendrocytic basic protein (MBOP) In the control patient, although antibodies specific for common and ubiquitous human pathogens including influenza virus and Streptococcus pneumonia are detected, no antibodies specific for myelin proteins and peptides are detected. In MS patient 1, antigen arrays detect autoantibodies specific for whole myelin basic protein (MBP), whole myelin oligodendrocyte protein (MOG), as well as autoantibodies recognizing MOG peptide 35-55, MBP peptide 1-20, and MBP peptide 68-86. In contrast, in MS patient 2 autoantibodies are detected against MOG protein and MOG peptide 25-42. In MS patient 3, autoantibodies specific for proteolipid protein (PLP) peptide 139-151 are identified.

FIGS. 4A to 4C shows an antibody specificity profile including an antigen array characterization (antigen array profile) of the diversity and similarities of the autoantibody response in mice with experimental autoimmune encephalomyelitis (EAE). 2400-spot 'myelin proteome' arrays were produced by spotting putative myelin antigens using a robotic microarrayer, probed with EAE mouse serum followed by Cy-3-labeled anti-mouse Ig secondary antibody, scanned using a GenePix scanner, and images analyzed using GenePix software to determine levels of autoantibody binding to each spot. A-C represent scanned images of arrays probed with serum from a control mouse (A) and 2 SJL mice 87 days post-EAE induction with PLPp139-151 that developed relapsing disease (B&C). Autoantibody reactivity against the inducing peptide PLPp139-151 is significantly stronger in the 2 mice with EAE relative to the control, autoantibody reactivity against an adjacent intra-molecular epitope PLPp89-106 is observed in mouse-2 but not mouse-1 or the control, and autoantibody reactivity against inter-molecular proteins and epitopes including MOG protein, MOGp66-78, CNPase p343-373, and MBPp1-20 are observed in both mice with EAE but not the control. Results were confirmed by ELISA and are representative of autoantibody reactivity observed in additional mice. Thus, SJL mice induced with PLP peptide 139-151 undergo spreading of their autoimmune response to adjacent peptide epitopes on PLP as well as to epitopes on 3 additional myelin proteins including MBP, MOG, and CNPase. These results demonstrate antigen array identification of the specific autoantigens targeted by the autoantibody response. Antigen-specific DNA tolerizing vaccines encoding a greater number of the antigen array-identified targets of the autoantibody response had greater efficacy for preventing and treating EAE than vaccines encoding a single of the autoantibody targets or non-targeted myelin antigens.

FIGS. 5A and 5B shows an antibody specificity profile including an antigen array characterization (antigen array profile) of the autoantibody response in mice with collagen-induced arthritis (CIA). Antigen arrays were generated using a robotic capillary arrayer to spot putative synovial peptide and protein autoantigens in RA into ordered arrays on poly-L-lysine-coated microscope slides. Spotted antigens include collagens type I, II, and III, CIIp257-270, Ro52, La, histidyl-tRNA synthetase (Jo-1), the 70 kDa and C component of the U1 small nuclear ribonucleoprotein complex (U1-70 kDa, U1snRNP-C), hnRNP-B1, and overlapping peptides for GP-39. We spotted antibodies pre-labeled with Cy-3 as 'marker features' to orient the arrays (the vast majority of the green features). Arrays were incubated with (a) normal DBA/1LacJ serum or (b) serum obtained at disease onset (day 29) from a DBA/1LacJ mouse induced to develop CIA with chick CII in CFA. Bound antibodies were detected using Cy-3-conjugated donkey-anti-mouse IgM/IgG. Autoantibodies specific for CII and CIIp257-270 are detected only in the CIA serum sample.

FIG. 6 provides cluster analysis demonstrating that DNA tolerizing therapy encoding multiple epitopes from the antigen array identified autoantigens in EAE reduces clinical disease activity and reduces spreading of the autoimmune response. Individual mice are listed on the X axis, and peptide and protein antigens present on the 'myelin proteome' array on the Y axis. Green indicates lack of reactivity, and red indicates autoantibody reactivity. The cluster analysis algorithm groups mice based on similarities in the antigen array determined specificity of their autoantibody responses. This image represents a small region of the overall cluster. Normal mice (NMS) cluster and the predominance of green indicates lack of autoantibody reactivity to the listed antigens. SJL mice with chronic relapsing EAE treated with control vector or buffer (B and C) cluster and have significant autoantibody reactivity, indicated by red, against various myelin antigens. This observed spreading of the autoantibody response in these mice correlates with their more severe disease course, with an average of 2.4-3.5 relapses over the 87 day period. The average number of clinical exacerbations of paralysis (relapses) are presented at the top of the figure by the numbers over the bars indicating the relevant group of mice. In contrast, mice treated with the myelin protein cocktail DNA tolerizing vaccine (containing a large number of the antigen array identified targets of the autoimmune response, and demonstrating the greatest efficacy in treating EAE [Table 4]) cluster and have a significant reduction in the spreading of their autoantibody response as indicated by the increased green relative to the other groups. This reduction in spreading of the autoimmune response correlated with their less-severe clinical course with an average of 1.5 relapses over the 87 day period.

DETAILED DESCRIPTION OF THE EMBODIMENTS

In one embodiment, high throughput determination is made of disease relevant antibodies present in patient serum by detailed binding analyses of these antibodies. The antibody specificity profile reveals the individual's immune response to multiple epitopes of autoantigens, allergens, graft antigens, etc. Such antibody or antigen specificity profiles are used in the development of individualized diagnosis and treatment of immune associated disease, including autoimmune diseases, allergies and graft rejection. By tracking epitope spreading, antigen specificity, and quantitative binding data the staging and progression of disease can be determined.

It has been found that the specificity of the autoantibody response can correlate with that of the autoreactive T cell response. In several human autoimmune diseases the autoimmune T and B cell responses recognize the same immunodominant epitopes. In those cases where there is discordance between the fine specificity of the B and T cell responses in an autoimmune disease, the ability to identify the specific self-protein(s) against which an individual is autoreacting can be sufficient to study the specificity and evolution of the autoimmune response and to select appropriate antigen-specific treatment. Knowledge of the specificity of the autoantibody response in individual patients can facilitate early diagnosis, serve as a prognostic indicator, and help guide development and selection of the appropriate antigen-specific tolerizing therapy.

For certain autoimmune diseases, including autoimmune diabetes, systemic lupus erythematosus (SLE), myasthenia gravis, and Grave's disease, the detection of antibody reactivity against one or two self-proteins has diagnostic utility. Certain antibody reactivities have also been demonstrated to have prognostic utility. For example, autoantibodies directed against DNA are pathogenic in some models of SLE, are generally associated with renal involvement, and their titers frequently correlate with disease activity. In polymyositis, Jo-1 autoantibodies frequently predate clinical disease by months to years, and predict development of interstitial lung disease and a poor prognosis.

Human autoimmune disease is extremely heterogenous in terms of its clinical manifestations. For example, patients with SLE have a spectrum of clinical disease that varies from patient to patient. Certain patients have disease that primarily involves their skin and joint manifestations, while others have disease that causes fluid accumulation on the heart and lungs (serositis), while others have disease that primarily affects the kidneys and brain. In multiple sclerosis, certain patient have relapsing-remitting disease that follows a benign course with no disability, others initially have relapsing-remitting disease that evolves to chronic progressive disease causing paralysis and disability, while yet another groups develops chronic-progressive disease from the onset. It is likely that the different clinical forms of each of these diseases represent distinct subtypes of disease, in which the autoimmune response is directed against different autoantigens and which will differentially respond to specific therapies.

In one embodiment of the invention, the antibody specificity profiles are determined through the binding of antibodies from a patient sample to antigen(s) comprising an array, where the peptides correspond to potential epitopes of antigens. Small amounts of the sample are sufficient to screen a large number of different peptides. The array may comprise individual spots of protein complexes, whole proteins and/or fragments of proteins, where the fragments may be overlapping peptides that encompass the complete protein, or a partial representation of the protein, which may include known immunodominant peptides. The array may also comprise spots of other molecules including single stranded DNA, double stranded DNA, oligonucleotides, RNA, lipids, carbohydrates, or other molecules. In the case of autoimmune disease the antibody specificity profile provides a means of monitoring and/or predicting the antibody response to antigen-specific vaccines or treatments, which vaccines or treatments may be DNA-based, peptide-based, protein-based or based on other molecules. The antibody response profile can indicate whether efficacious therapy has been delivered to the patient.

The information obtained from the antibody specificity profile is used to monitor treatment, modify therapeutic regimens, and to further optimize the selection of therapeutic agents. With this approach, therapeutic and/or diagnostic regimens can be individualized and tailored according to the specificity data obtained at different times over the course of treatment, thereby providing a regimen that is individually appropriate. In addition, patient samples can be obtained at any point during the treatment process for analysis.

Mammalian species that provide samples for analysis include canines; felines; equines; bovines; ovines; etc. and primates, particularly humans. Animal models, particularly small mammals, e.g. murine, lagomorpha, etc. may be used for experimental investigations. Animal models of interest include those for models of autoimmunity, graft rejection, and the like.

Antibodies, Autoantibodies and T Cell Receptors: The antigenic specificity of the immune system is provided by the group of proteins known as antibodies (or immunoglobulins) and T cell receptors. Each is produced in a variety of classes, subclasses and isotypes, which are all well known in the art and are included in this definition for the purposes of the invention. Through processes of genetic recombination, and in some cases somatic mutation, a very large repertoire of different protein sequences is generated in the variable regions of these proteins. The non-covalent binding interaction of these variable regions enables the immune system to bind to antigens, which are molecules such as polysaccharides, polypeptides, polynucleotides, etc. The "specificity" of an antibody or T cell receptor therefore refers to the ability of the variable region to bind with high affinity to an antigen.

The binding site of antibodies typically utilizes multiple non-covalent interactions to achieve high affinity binding. While a few contact residues of the antigen may be brought into close proximity to the binding pocket, other parts of the antigen molecule can also be required for maintaining a conformation that permits binding. The portion of the antigen bound by the antibody is referred to as an epitope. As used herein, an epitope is that portion of the antigen which is sufficient for high affinity binding. Where the antigen is a protein, generally a linear epitope will be at least about 7 amino acids in length, and not more than about 15 to 22 amino acids in length. However, antibodies may also recognize conformational determinants formed by non-contiguous residues on an antigen, and an epitope can therefore require a larger fragment of the antigen to be present for binding, e.g. a protein or ribonucleoprotein complex domain, a protein domain, or substantially all of a protein sequence. In other instances, e.g. haptens, the epitope can be a very small molecule, e.g. digoxin, digoxigenin, etc. Autoantibodies are also well established to bind complexes of proteins, lipids, nucleic acids, or nucleoprotein complexes in systemic lupus erythematosus and other autoimmune diseases. In addition, autoantibodies can be directed against post-translational-modifications on self proteins. Self protein as used herein are proteins encoded within the genome and produced by the organism. Examples of post-translational modifications against which autoantibodies have been detected include phosphorylated and citrulline-modified amino acids as well as differences in glycosylation. In certain diseases autoimmune responses are directed against DNA, RNA, lipid and other molecules.

The level of affinity of antibody binding that is considered to be "specific" will be determined in part by the class of antibody, e.g. antigen specific antibodies of the IgM class may have a lower affinity than antibodies of, for example, the IgG classes. As used herein, in order to consider an antibody interaction to be "specific", the affinity will be at least about $10^{-7}$ M, usually about $10^{-8\ to\ -9}$ M, and may be up to $10^{-11}$ or higher for the epitope of interest. It will be understood by those of skill in the art that the term "specificity" refers to such a high affinity binding, and is not intended to mean that the antibody cannot bind to other molecules as well. One may find cross-reactivity with different epitopes, due, e.g. to a relatedness of antigen sequence or structure, or to the structure of the antibody binding pocket itself. Antibodies demonstrating such cross-reactivity are still considered specific for the purposes of the present invention.

The T cell receptor recognizes a more complex structure than antibodies, and requires both a major histocompatibility antigen binding pocket and an antigenic peptide to be present. The binding affinity of T cell receptors is lower than that of antibodies, and will usually be at least about $10^{-4}$ M, more usually at least about $10^{-5}$ M.

Autoreactive antibodies, or autoantibodies, and T cell receptors are those antigen receptors that bind with high affinity to molecules present in the host, usually molecules that are normally present in the host, e.g. in autoimmune disease or tumor antigens in the case of certain cancers. Antigens present from grafts of foreign tissue are generally not considered to be autoantigens. The initiating immunogen may be the autoantigen, or may be a cross-reactive molecule with the autoantigen.

The disclosed method is in part based on the correlation of the specificity of the autoantibody response with that of the autoreactive helper T cell response, which drives autoimmune responses. In several human autoimmune diseases the autoimmune T and B cell responses recognize the same immunodominant epitopes. The immunodominant myelin basic protein (MBP) epitope is recognized by both autoreactive T and B cells in MS. Even in those cases where there is a discordance between the fine specificity of the B and T cell responses, the ability to identify the specific self-protein(s) against which an individual is autoreacting is sufficient to guide selection of antigen-specific tolerizing therapy.

Arrays: An array is a collection of addressable elements. Such elements can be spacially addressable, such as arrays contained within microtiter plates or printed on planar surfaces where each element is present at distinct X and Y coordinates. Alternatively, elements can be addressable based on tags, beads, nanoparticles, or physical properties. The microarrays can be prepared according to the methods known to the ordinarily skilled artisan (See for example, U.S. Pat. No. 5,807,522; Robinson et al. (2002) Nature Medicine 8:295-301; Robinson et al. (2002) 46:885-93). Arrays as used herein refers to any biologic assay with multiple addressable elements. In one embodiment the addressable elements are antigens. In another embodiment the addressable elements are epitopes. A microarray is a miniaturized form of an array. As used herein, elements refer to any antigen that can be bound by an antibody. Antigen as used herein refer to any molecule that can bind specifically to an antibody. Molecules can be, but are not limited to, proteins, polypeptides, peptides, RNA, DNA, lipids, glycosylated molecules, carbohydrates, polypeptides with phosphorylation modifications, and polypeptides with citrulline modifications, aptamers, oxidated molecules, other molecules, and other molecules.

Addressability: For the elements described herein, addressibility refers to the location, position, tags, cleavable tags or markers, identifiers, spectral properties, electrophoretic properties, or other physical properties that enable identification of the element. One example of addressability, also known as coding, is spatial addressability, where the position of the molecule is fixed, and that position is correlated with the identity. This type of spatial array is generally synthesized or spotted onto a planar substrate, producing, for example, microarrays, where a large number of different molecules are densely laid out in a small area, e.g. comprising at least about 400 different sequences per $cm^2$, and may be 1000 sequences per $cm^2$, or as many as 5000 sequences per $cm^2$, or more. Less dense arrays, such as may be found in ELISA or RIA plates where wells in a plate each contain a distinct antigen, may comprise from about 96 sequences per plate, up to about 100 sequences per $cm^2$, up to the density of a microarray. Other spatial arrays utilize fiber optics, where distinct antigens are bound to fibers, which can then be formed into a bundle for binding and analysis. Methods for the manufacture and use of spatial arrays of polypeptides are known in the art. Recent articles include Joos et al. (2000) *Electrophoresis* 21(13): 2641-50 describing a microarray-based immunoassay containing serial dilutions of antigens; Roda et al. (2000) *Biotechniques* 28(3):492-6 describing a system obtained by adapting a commercial ink-jet printer and used to produce mono- and bidimensional arrays of spots containing protein on cellulose paper; and Ge (2000) *Nucleic Acids Res* 28(2):e3 describing a universal protein array system for quantitative detection of protein-protein, protein-DNA, protein-RNA and protein-ligand interactions. See also, Mendoza et al. (1999) "High-throughput microarray-based enzyme-linked immunosorbent assay (ELISA)" *Biotechniques* 27:778-780; and Lueking et al. (1999) "Protein microarrays for gene expression and antibody screening" *Anal. Biochem.* 270:103-111.

An alternative to this type of spatial coding array is the use of molecular "tags," where the target antigens or epitopes are attached to a detectable label, or tag, which provides coded information about the sequence of the antigen or epitope. In certain cases these tags can be cleaved from the element, and subsequently detected to identity the element. In another embodiment, a set of antigens or epitopes may be synthesized or attached to a set of coded beads, where each bead is linked to a distinct antigen or epitope, and where the beads are themselves coded in a manner that allows identification of the attached antigen or epitope. The use of a multiplexed microsphere set for analysis of clinical samples by flow cytometry is described in International Patent application no. 97/14028; and Fulton et al. (1997) *Clinical Chemistry* 43:1749-1756). It is also possible to use other addressable particles or tags (reviewed in Robinson et al. (2002) *Arthritis Rheumatism* 46:885-93).

In this type of "tag array," where the antigen is bound to beads or microspheres, one may utilize flow cytometry for detection of binding. For example, microspheres having fluorescence coding have been described in the art, where the color and level of fluorescence uniquely identifies a particular microsphere. The antigen is thus covalently attached to a "color coded" object. A labeled antibody can be detected by flow cytometry, and the coding on the microsphere used to identify the bound antigen.

Antigen Array: One embodiment of an array is an antigen array. An antigen array as used herein, refers to a spatially separated set of discrete molecular entities capable of binding to antibodies which are arranged in a manner that allows identification of the specificity of the antibodies contained within the patient sample. In other words, a set of target antigens having distinct sequences, three dimensional shapes, or molecular structures, where each target antigen is coded for identification. The array may comprise one or more of proteins, polypeptides, peptides, RNA, DNA, lipid, glycosylated molecules, polypeptides with phosphorylation modifications, and polypeptides with citrulline modifications, aptamers, other molecules, and other molecules, where different classes of molecules may be combined in an array.

Antigens: Antigens include molecules such as nucleic acids, lipids, ribonucleoprotein complexes, protein complexes, proteins, polypeptides, peptides and naturally occurring modifications of such molecules against which an immune response involving T and B lymphocytes can be generated. For each antigen, there exists a panel of epitopes that represent the immunologic determinants of that antigen. Antigens include any molecule that can be recognized, all or in part, by an antibody or T cell receptor. As used herein include antigens associated with autoimmune disease, allergy or tissue transplant rejection. With regard to autoimmune disease, the antigens herein are often referred to as autoantigens. With regard to allergic disease the antigens herein are often referred to as allergens. Antigens comprise immunologic epitopes.

Epitopes: Epitopes are portions of antigens that are recognized by B lymphocytes, and specifically by the antibodies expressed on the cell surface and secreted by B cells. Epitopes can also be recognized by specific receptors on T lymphocytes. An individual antigen typically contains multiple epitopes, although there are instances in which an antigen contains a single epitope. In one embodiment of this invention, peptide fragments derived from a whole protein antigen are used to represent individual epitope(s) targeted by the antibodies produced by B cells. In another embodiment, portions of molecules representing post-translational modifications, carbohydrates, lipids and other molecules can be used to represent individual epitopes. Epitopes represent shapes recognized by immune B and T cells, and can also be represented by non-antigen derived peptides and other molecules that possess the same epitope shape that is present within the native antigen. An example of an element with an epitope shape is an aptamer. An aptamer is a molecule that provides a shape that can mimic an immunologic epitope. Using a plurality of aptamers a library of epitope shapes can be generated.

For the purposes of the invention, arrays of autoantigens and autoantigen-derived epitopes can be used to determine a patient's antibody specificity profile for the identification or determination of: 1. patients likely to develop disease; 2. patients likely to develop more or less severe disease; 3. patients likely to respond to a particular therapy, or to have an adverse event related to a particular therapy; 4. patient-specific therapy; and, 5. whether a particular therapeutic intervention has been successful, unsuccessful, or detrimental. An autoantigen array comprises the various autoantigens either known to be associated with disease, suspected to be associated with a particular disease, or a library of potential autoantigens. An autoantigen array, in one instance may include autoantigens optimized for a particular disease, while in another instance may include a library of unknown antigens to identify targets of the antibody response in patients with a disease. An autoantigen array consisting of panels of autoantigens may be used for screening purposes, where the panel reflects the different epitopes associated with a particular disease. Antigen epitope panels of interest include panels optimized for specific diseases of interest, which may include one or more whole proteins, peptide and overlapping peptides within the sequence of these proteins, and peptides representing dominant epitopes. The term polypeptide, as used herein, designates any of proteins and peptides. Where short peptides are used, preferred peptides are at least about 7 amino acids in length, may be at least about 15 amino acids in length, and as many as 22 amino acids in length. The peptides may be overlapping by 7-10 amino acids, and can encompass the whole sequence of the protein of interest. The peptide can also be a mimic of a native peptide shape, for example a cyclic peptide, nucleic acid aptamer, or can be another molecule, drug, or organic molecule that mimics the 3 dimensional shape recognized by the antibody or T cell receptor molecule Immunologic epitope: Immunologic epitope is the portion of any peptide, polypeptide, protein, lipid, carbohydrate or other molecule that is recognized by an antibody or T cell receptor.

Autoantigens: are any molecule produced by the organism that can be the target of an immunologic response. In one aspect, such molecule are peptides, polypeptides, and proteins encoded within the genome of the organism. In another aspect, such molecule are post-translationally-generated modifications of these peptides, polypeptides, and proteins, such as cleavage, phosphorylation, deimination of arginine to citrulline, and other modifications generated through physiologic and non-physiologic cellular processes. In yet another aspect, such molecules include carbohydrates, lipids and other molecules produced by the organism. Examples of autoantigens as used herein, include endogenous proteins or fragments thereof that elicit a pathogenic immune response. Of particular interest are autoantigens that induce a T cell mediated pathogenic response. Autoimmune diseases characterized by the involvement of T cells include multiple sclerosis, experimental autoimmune encephalitis, rheumatoid arthritis, insulin dependent diabetes mellitus, etc.

For the purposes of the invention, panels of autoantigens or autoantigen epitopes may be used for screening purposes, where the panel reflects the different epitopes associated with a particular disease. Antigen epitope panels of interest include panels optimized for specific diseases of interest, which may include one or more of whole proteins, peptide and overlapping peptides within the sequence of these proteins, and peptides representing dominant epitopes. The term polypeptide, as used herein, designates any of proteins and peptides. Where short peptides are used, preferred peptides are at least about 7 amino acids in length, may be at least about 15 amino acids in length, and as many as 22 amino acids in length. The peptides may be overlapping by 7-10 amino acids, and can encompass the whole sequence of the protein of interest.

Antigen arrays contain panel(s) of antigens representing self-proteins, modifications of these self-proteins, and other molecules present in tissues targeted by autoimmune diseases or the aberrant immune response in tissue transplant rejection.

Usually a panel or an array of antigens will comprise one or more different antigenic molecules, i.e. a protein, lipid, polysaccharide, polynucleotide molecule, and will usually comprise two or more different antigens, more usually three or more antigens, and may comprise as many as five to ten different antigens, or more. Each antigen may be represented by one or more different epitopes, usually three or more different epitopes, more usually five or more, and may be as many as ten to twenty different epitopes.

Examples of arrays for specific diseases are; antigen panels or arrays for demyelinating diseases, such as multiple sclerosis and EAE, and may comprise antigens and/or epitopes from proteolipid protein (PLP); myelin basic protein (MBP); myelin oligodendrocyte protein (MOG); cyclic nucleotide phosphodiesterase (CNPase); myelin-associated glycoprotein (MAG), and myelin-associated oligodendrocytic basic protein (MBOP); alpha-B-crystalin (a heat shock protein); viral and bacterial mimicry peptides, e.g. influenza, herpes viruses, hepatitis B virus, etc.; OSP (oligodendrocyte specific-protein); citrulline-modified MBP (the C8 isoform of MBP in which 6 arginines have been de-imminated to citrulline), etc. The integral membrane protein PLP is a dominant autoantigen of myelin. Determinants of PLP antigenicity have been identified in several mouse strains, and include residues 139-151, 103-116, 215-232, 43-64 and 178-191. At least 26 MBP epitopes have been reported (Meinl et al. (1993) *J. Clin. Invest.* 92:2633-2643). Notable are residues 1-11, 59-76 and 87-99. Immunodominant MOG epitopes that have been identified in several mouse strains include residues 1-22, 35-55, 64-96.

Panels or arrays may be specific for a disease, e.g. multiple sclerosis, arthritis, SLE, etc., for a class of diseases, e.g. transplant related disorders, allergic disorders, etc., or may be a broad based antigenic panel or array for multiple diseases.

Disease associated antigens: Disease-associated antigens, are antigens known to be associated with, or are not currently known to be associated with but ultimately shown to be associated with, an immune-related disease. Examples of autoimmune disease associated antigens are described below. Antigen panels or arrays for demyelinating diseases, such as multiple sclerosis and EAE, may comprise epitopes from proteolipid protein (PLP); myelin basic protein (MBP); myelin oligodendrocyte protein (MOG); cyclic nucleotide phosphodiesterase (CNPase); myelin-associated glycoprotein (MAG), and myelin-associated oligodendrocytic basic protein (MBOP); alpha-B-crystalin (a heat shock protein); viral and bacterial mimicry peptides, e.g. influenza, herpes viruses, hepatitis B virus, etc.; OSP (oligodendrocyte specific-protein); citrulline-modified MBP (the C8 isoform of MBP in which 6 arginines have been de-imminated to citrulline), etc. The integral membrane protein PLP is a dominant autoantigen of myelin. Determinants of PLP antigenicity have been identified in several mouse strains, and include residues 139-151, 103-116, 215-232, 43-64 and 178-191. At least 26 MBP epitopes have been reported (Meinl et al. (1993) *J. Clin. Invest.* 92:2633-2643). Notable are residues 1-11, 59-76 and 87-99. Immunodominant MOG epitopes that have been identified in several mouse strains include residues 1-22, 35-55, 64-96.

Antigen panels or arrays for insulin dependent diabetes mellitus may comprise the antigens and epitopes derived from IA-2; IA-2beta; GAD; insulin; proinsulin; HSP; glima 38; ICA69; and p52.

Panels or arrays for rheumatoid arthritis may comprise epitopes from type II collagen; hnRNP; A2/RA33; Sa; filaggrin; keratin; citrulline; cartilage proteins including gp39; collagens type I, III, IV, V, IX, XI; HSP-65/60; IgM (rheumatoid factor); RNA polymerase; cardiolipin; aldolase A; citrulline-modified filaggrin and fibrin, etc. Autoantibodies that recognize filaggrin peptides containing a modified arginine residue (deiminated to form citrulline) have been identified in the serum of a high proportion of RA patients. Autoreactive T and B cell responses are both directed against the same immunodominant type II collagen (CII) peptide 257-270 in some patients.

Antigen panels or arrays for systemic lupus erythematosus (SLE) may include DNA; phospholipids; nuclear antigens; Ro; La; U1 ribonucleoprotein; Ro60 (SS-A); Ro52 (SS-A); La (SS-B); calreticulin; Grp78; Scl-70; histone; Sm protein; and chromatin, etc.

Antigen panels or arrays for autoimmune uveitis may include S-antigen, and interphotoreceptor retinoid binding protein (IRBP), etc.

Antigen panels or arrays for myasthenia gravis may include epitopes with the acetylcholine receptor. For Grave's disease epitopes may include the Na+/I− symporter; thyrotropin receptor; Tg; and TPO. Sjogren's syndrome panels may include SSA (Ro); SSB (La); and fodrin. Panels for pemphigus vulgaris may include desmoglein-3. Panels for myositis may include tRNA synthetases (e.g., threonyl, histidyl, alanyl, isoleucyl, and glycyl); Ku; PM/Scl; SSA; U1 sn-ribonuclear protein; Mi-1; Mi-1; Jo-1; Ku; and SRP. Panels for scleroderma may include Scl-70; centromere proteins; U1 ribonuclear proteins; and fibrillarin. Panels for primary biliary cirrhosis may include pyruvate dehydrogenase E2 and alpha-ketoglutarate dehydrogenase components. Panels for pernicious anemia may include intrinsic factor; and glycoprotein beta subunit of gastric H/K ATPase.

Autoantibodies: Autoantibodies are any antibody that recognizes or binds a self-antigen or self-epitope. Self-antigens or self-epitopes include polypeptides, proteins, peptides, lipids, polysaccharides, and modifications of these self-antigens that are encoded within the genome or produced within an organism.

Allergens are immunogenic compounds that cause an enhanced Th2-type T cell response and IgE B cell response in a susceptible individual, including asthma associated allergens. Allergens of interest include antigens found in food, such as strawberries, peanuts, milk proteins, egg whites, etc. Other allergens of interest include various airborne antigens, such as grass pollens, animal danders, house mite feces, etc. Molecularly cloned allergens include *Dermatophagoides pteryonyssinus* (Der P1); Lol pl-V from rye grass pollen; a number of insect venoms, including venom from jumper ant *Myrmecia pilosula; Apis mellifera* bee venom phospholipase A2 ($PLA_2$ and antigen 5S; phospholipases from the yellow jacket *Vespula maculifrons* and white faced hornet *Dolichovespula maculata*; a large number of pollen proteins, including birch pollen, ragweed pollen, Parol (the major allergen of *Parietaria officinalis*) and the cross-reactive allergen Parjl (from *Parietaria judaica*), and other atmospheric pollens including *Olea europaea, Artemisia* sp., gramineae, etc. Other allergens of interest are those responsible for allergic dermatitis caused by blood sucking arthropods, e.g. Diptera, including mosquitoes (*Anopheles* sp., *Aedes* sp., *Culiseta* sp., *Culex* sp.); flies (*Phlebotomus* sp., *Culicoides* sp.) particularly black flies, deer flies and biting midges; ticks (*Dermacenter* sp., *Ornithodoros* sp., *Otobius* sp.); fleas, e.g. the order Siphonaptera, including the genera *Xenopsylla, Pulex* and *Ctenocephalides felis felis*. The specific allergen may be a polysaccharide, fatty acid moiety, protein, etc.

Methods of Specificity Analysis

Immune related diseases include: 1. autoimmune diseases in which the immune response aberrantly attacks self-antigens, examples of which include but are not limited to multiple sclerosis (MS), rheumatoid arthritis (RA), type I autoimmune diabetes (IDDM), and systemic lupus erythematosus (SLE); 2. allergic diseases in which the immune system aberrantly attacks molecules such as pollen, dust mite antigens, bee venom, peanut oil and other foods, etc.; and 3. tissue transplant rejection in which the immune system aberrantly attacks antigens expressed or contained within a grafted or transplanted tissue, such as blood, bone marrow cells, or solid organs including hearts, lungs, kidneys and livers. Samples are obtained from patients with clinical symptoms suggestive of an immune-related disease or with an increased likelihood for developing such a disease based on family history or genetic testing.

Formats for human patient sampling include time courses that follow the progression of disease, comparisons of different patients at similar disease stages, e.g. early onset, acute stages, recovery stages, etc.; tracking a patient during the course of response to therapy, including drug therapy, vaccination and the like. Data from animals, e.g. mouse, rat, rabbit, monkey, etc. may be compiled and analyzed in order to provide databases detailing the course of disease, antigens involved in diseases, etc. Biological samples from which patient antibodies may be collected include blood and derivatives therefrom, e.g. serum, plasma, fractions of plasma, etc. Other sources of samples are body fluids such as synovial fluid, lymph, cerebrospinal fluid, bronchial aspirates, and may further include saliva, milk, urine, and the like. Both antibodies and T cell receptors may also be obtained from the appropriate lymphocytes, which may be collected from blood, tissues such as spleen, thymus, lymph nodes, fetal liver, tissues at the site of autoimmune lesions, e.g. pancreas, joints, kidneys, cerebrospinal fluid, etc. The lymphocytes may be analyzed intact, or lysates may be prepared for analysis. Patient samples contain antibodies, and antigen arrays are used to profile these antibodies.

In a typical assay, a patient sample containing antibodies is physically contacted with the antigen array, under conditions that permit high affinity binding, but that minimize non-specific interactions. In one embodiment, patient samples are pippeted onto the array or into a space containing the addressable elements. The array is washed free of unbound material, and the presence of bound antibodies is detected, and correlated with the cognate antigen.

The means for identifying the disease-associated antigens within the array that bind to the antibodies within the patient sample utilize methods for detection that are known in the art. Those methods of identification may include pre-labeling the sample directly or indirectly; adding a second stage antibody that binds to the antibodies or to an indirect label, e.g. labeled goat anti-human serum, rat anti-mouse, and the like. Other methods of identification include analysis of addressable elements such as beads, nanoparticles, tags, cleavable tags and other physical properties of or conferred upon the elements within the array. Varying concentrations of a single epitope may be present in order to facilitate quantitation of the bound antibody.

Useful labels include fluorochromes, e.g. Cy2, Cy3, Cy5, fluorescein isothiocyanate (FITC), rhodamine, Texas Red, phycoerythrin, allophycocyanin, 6-carboxyfluorescein (6-FAM), 2',7'-dimethoxy-4',5'-dichloro-6-carboxyfluorescein (JOE), 6-carboxy-X-rhodamine (ROX), 6-carboxy-2',4', 7',4,7-hexachlorofluorescein (HEX), 5-carboxyfluorescein (5-FAM) or N,N,N',N'-tetramethyl-6-carboxyrhodamine (TAMRA)). Indirect labels include haptens, such as digoxin and digoxigenin, biotin, etc., where a second stage binding partner, e.g. avidin, anti-digoxin antibody, etc., may be labeled with an enzyme, e.g. horseradish peroxidase, fluorochrome, radioactive label, etc. Preferably, where a control sample is included, the fluorescent reporter used to label the control sequences emits a fluorescent signal at an excitation and/or emission wavelength detectably distinct from that of the fluorescent reporter used to label the test sequence.

Detection may also occur using methods that do not require labeling. Examples include detection of changes in charge or mass of the bound self-antigen using methods or devices such as single electron transistors, proteins applied to carbon nanotubes or meshworks of nanotubes, surface plasmon resonance, atomic force microscopy, and other methods known to those skilled in the art.

Generally assays will include various negative and positive controls, as known in the art. These may include positive controls of "spiked" samples with known autoantibodies, patients with known disease, and the like. Negative controls include samples from normal patients, animal serum, and the like.

Binding of the antibody containing sample to an antigen array is accomplished according to methods well known in the art. The binding conditions and washes are preferably carried out under conditions that allow only high affinity binding partners to be retained.

Two-color labeling of different antibodies can be utilized in binding to the same or to separate arrays, in order to assay the level of binding in a patient sample compared to a control sample. From the ratio of one color to the other, for any particular array element, the relative abundance of antibodies with a particular specificity in the two samples can be determined. In addition, comparison of the binding of the two samples provides an internal control for the assay. Competitive assays are well known in the art, where a competing antibody of known specificity, or an epitope containing molecule, may be included in the binding reaction.

Arrays can be scanned to detect binding of antibodies, e.g. using a scanning laser microscope as described in Shalon et al., *Genome Res.* 6:639 (1996). A separate scan, using the appropriate excitation line, is performed for each of the fluorophores used. The digital images generated from the scan are then combined for subsequent analysis. For any particular array element, the ratio of the signal from one sample is compared to the fluorescent signal from the other sample, and the relative abundance determined.

Various methods are used to determine the antibody specificity profile from a patient sample. An antibody specificity profile is initially determined for an individual patient, and as used herein is means the antigens or epitopes that are bound by the antibodies from a patient sample. The comparison of a binding pattern obtained from a patient sample and a binding pattern obtained from a control, or reference, sample is accomplished by the use of suitable deduction protocols, AI systems, statistical comparisons, pattern recognition algorithms, etc. Typically a data matrix is generated, where each point of the data matrix corresponds to a readout from specific array or antigens or epitopes. The information from reference patterns can be used in analytical methods to determine antigen or epitope spreading, relative abundance, changes over time, changes in antibody isotype produced, and other related changes.

The antigen or epitope readout may be a mean, average, median or the variance or other statistically or mathematically-derived value associated with the measurement. The antigen or epitope readout information may be further refined by direct comparison with the corresponding reference or control pattern. A binding pattern may be evaluated on a number of points: to determine if there is a statistically significant change at any point in the data matrix; whether the change is an increase or decrease in the epitope binding; whether the change is specific for one or more physiological states, and the like. The absolute values obtained for each epitope under identical conditions will display a variability that is inherent in live biological systems and also reflects individual antibody variability as well as the variability inherent between individuals.

Classification rules for identifying reference patterns will be constructed from sets of training data (i.e. data matrices) obtained from multiple repeated experiments. Classification rules will be selected when they correctly identify repeated reference patterns and successfully distinguish distinct reference patterns. Classification rule-learning algorithms may include decision tree methods, statistical methods, naive Bayesian algorithms and the like.

In order for novel test patterns to be effectively identified and classified, the knowledge database must be of sufficient complexity. This can be accomplished by several approaches for generating a sufficiently encompassing set of classification patterns, and sufficiently powerful mathematical/statistical methods for discriminating between them.

In one embodiment, the information obtained from analysis of serum and other pathologic tissue samples is used to refine and build a database of antibody specificity profiles. For example, the identification of specific binding moieties may be used to track disease and develop therapeutics.

Patient antibody specificity profile: Antibody specificity profile as used herein refers to the antigen or epitope array-determined spectrum of antigens or epitopes recognized by the antibodies derived from a patient sample.

Once the subset of specificities for a particular sample are identified, the data is used in developing new diagnostic agents, and in selecting the most appropriate therapy for an individual. By analysis of autoantibody specificity on an individual basis, the specific epitope targets that are present in the disease state are determined. One or more therapeutic agents can then be selected, which have the best specificity for the individual patient and disease.

Conditions for Analysis and Therapy

Rheumatoid arthritis (RA) is a chronic autoimmune inflammatory synovitis affecting 0.8% of the world population. Current therapy for RA utilizes therapeutic agents that non-specifically suppress or modulate immune function. Such therapeutics, including the recently developed TNFα antagonists, are not fundamentally curative, and disease activity rapidly returns following discontinuation of therapy. Tremendous clinical need exists for fundamentally curative therapies that do not cause systemic immune suppression or modulation.

Degenerative joint diseases may be inflammatory, as with seronegative spondyloarthropathies, e.g. ankylosing spondylitis and reactive arthritis; rheumatoid arthritis; gout; and systemic lupus erythematosus. The degenerative joint diseases have a common feature, in that the cartilage of the joint is eroded, eventually exposing the bone surface. Destruction of cartilage begins with the degradation of proteoglycan, mediated by enzymes such as stromelysin and collagenase, resulting in the loss of the ability to resist compressive stress. Alterations in the expression of adhesion molecules, such as CD44 (Swissprot P22511), ICAM-1 (Swissprot P05362), and extracellular matrix protein, such as fibronectin and tenascin, follow. Eventually fibrous coliagens are attacked by metalloproteases, and when the collagenous microskeleton is lost, repair by regeneration is impossible.

There is significant immunological activity within the synovium during the course of inflammatory arthritis. While treatment during early stages is desirable, the adverse symptoms of the disease may be at least partially alleviated by treatment during later stages. Clinical indices for the severity of arthritis include pain, swelling, fatigue and morning stiffness, and may be quantitatively monitored by Pannus criteria. Disease progression in animal models may be followed by measurement of affected joint inflammation. Therapy for inflammatory arthritis may combine the subject treatment with conventional NSAID treatment. Generally, the subject treatment will not be combined with such disease modifying drugs as cyclosporin A, methotrexate, and the like.

A quantitative increase in myelin-autoreactive T cells with the capacity to secrete IFN-gamma is associated with the pathogenesis of MS and EAE, suggesting that autoimmune inducer/helper T lymphocytes in the peripheral blood of MS patients may initiate and/or regulate the demyelination process in patients with MS. The overt disease is associated with muscle weakness, loss of abdominal reflexes, visual defects and paresthesias. During the presymptomatic period there is infiltration of leukocytes into the cerebrospinal fluid, inflammation and demyelination. Family histories and the presence of the HLA haplotype DRB1*1501, DQA1*0102, DQB1*0602 are indicative of a susceptibility to the disease. Markers that may be monitored for disease progression are the presence of antibodies in the cerebrospinal fluid, "evoked potentials" seen by electroencephalography in the visual cortex and brainstem, and the presence of spinal cord defects by MRI or computerized tomography. Treatment during the early stages of the disease will slow down or arrest the further loss of neural function.

Human IDDM is a cell-mediated autoimmune disorder leading to destruction of insulin-secreting beta cells and overt hyperglycemia. T lymphocytes invade the islets of Langerhans, and specifically destroy insulin-producing β-cells. The depletion of β cells results in an inability to regulate levels of glucose in the blood. Overt diabetes occurs when the level of glucose in the blood rises above a specific level, usually about 250 mg/dl. In humans a long presymptomatic period precedes the onset of diabetes. During this period there is a gradual loss of pancreatic beta cell function. The disease progression may be monitored in individuals diagnosed by family history and genetic analysis as being susceptible. The most important genetic effect is seen with genes of the major histocompatibility locus (IDDM1), although other loci, including the insulin gene region (IDDM2) also show linkage to the disease (see Davies et al, supra and Kennedy et al. (1995) *Nature Genetics* 9:293 □298).

Markers that may be evaluated during the presymptomatic stage are the presence of insulitis in the pancreas, the level and frequency of islet cell antibodies, islet cell surface antibodies, aberrant expression of Class II MHC molecules on pancreatic beta cells, glucose concentration in the blood, and the plasma concentration of insulin. An increase in the number of T lymphocytes in the pancreas, islet cell antibodies and blood glucose is indicative of the disease, as is a decrease in insulin concentration. After the onset of overt diabetes, patients with residual beta cell function, evidenced by the plasma persistence of insulin C-peptide, may also benefit from the subject treatment, to prevent further loss of function.

Allergy, or atopy is an increased tendency to IgE-based sensitivity resulting in production of specific IgE antibody to an immunogen, particularly to common environmental allergens such as insect venom, house dust mite, pollens, molds or animal danders. Allergic responses are antigen specific. The immune response to the antigen is further characterized by the over-production of Th2-type cytokines, e.g. IL-4, IL-5 and IL-10, by the responding T cells. The sensitization occurs in genetically predisposed people after exposure to low concentrations of allergen; cigarette smoke and viral infections may assist in the sensitization process.

Included in the group of patients suffering from atopy are those with asthma-associated allergies. About 40% of the population is atopic, and about half of this group develop clinical disease ranging from trivial rhinitis to life-threatening asthma. After sensitization, continuing exposure to allergens leads to a significant increase in the prevalence of asthma. Ninety per cent of children and 80% of adults with asthma are atopic. Once sensitization has occurred, re-exposure to allergen is a risk factor for exacerbations of asthma. Effective management of allergic asthma includes pharmacological therapy and allergen avoidance. The specific physiological effects of asthma associated allergies include airway inflammation, eosinophilia and mucus production, and antigen-specific IgE and IL-4 production.

In addition to allergies affecting human populations, non-human mammals are also known to suffer from allergic conditions. Fleas, *Ctenocephalides felis felis* and others, are now recognized as a major cause of physiological disorders among mammals. These insects are ectoparasites that attack dogs, cats, and humans. Certain species (i.e., dogs and cats), and individuals of these species are more allergic to fleabites than others, resulting in a clinical disorder called flea allergy dermatitis (FAD) or flea bite hypersensitivity. The hallmark of FAD is intense pruritis (itching) not only at the site of the flea bite but in a distinctive, body-wide distribution. This allergic reaction is a systemic response to a variety of protein substances in the oral secretions which the flea injects intradermally when it bites. Chronic FAD leads to scarring and permanent bald spots and is often associated with seborrhea, giving the dog a foul odor which pervades the household. Flea allergy also is recognized as a contributory cause of the common dermatitis of man known as papular urticaria.

Antigen Specific Therapeutic Methods

The antigens or epitopes recognized by the antibodies present in a patient sample, as described above, can be utilized to develop and select antigen or epitope specific therapies which comprise administration of an antigen or epitope specific therapeutic agent, where the agent is defined by binding of patient antibodies to the addressable elements on the array. The patient antibody specificity profile can be utilized to develop, select, and monitor responses to antigen or epitope specific therapeutic methods including: (1) oral administration of specific-antigens, termed 'oral tolerance' (Annu Rev Immunol. 12:809-37); (2) administration of native peptides (Science 258:1491-4; J Neurol Sci. 152:31-8); (3) administration of altered peptide ligands (Nature 379: 343-5); (4) administration of whole proteins (*Science* 263: 1139); administration of fusion-proteins or peptides; administration of other molecules, such as DNA or allergens including pollen, dust mites, cat salivary antigen (*J. Rheumatology* 28:257-65); administration of polynucleotide sequences encoding the targeted self-proteins or allergens (J. Immunol 162:3336-41; Curr. Dir. Autoimmun. 2:203-16). For all of these therapies, the antigens administered (or encoded in DNA) for purposes of immune suppression may comprise all or a portion of the epitopes identified by antibody. In one embodiment, one or more of the epitopes thus identified are administered, usually two or more, more usually three or more, and may comprise as many as ten or more different epitopes. Individual peptides or DNA encoding peptides may be administered. Alternatively, whole proteins, or DNA encoding all or substantially all of the antigenic protein may be administered. One or more, usually two or more, and as many as three of more different protein antigens may be thus administered. Antigen-specific therapy as used herein refers to a therapeutic regimen based upon an antigen specificity profile determined by the novel method of this invention.

In another embodiment of the invention, the knowledge based methods described above are used to identify patterns of disease, where a particular patient sample can be mapped to a pattern of disease progression. In such cases the suppressive epitopes may comprise not only epitopes currently recognized by patient antibodies, but may anticipate the progression of the disease and administer peptides that are likely to be disease-associated in a later stage of the disease, thus preventing the epitope spread observed in many autoimmune diseases.

In one embodiment, treatment comprises the induction of an antigen-specific, suppressive T-cell response by administration of a DNA expression cassette injected into host tissue, for example muscle or skin, for example as described in PCT application US00/0623. The vector comprises a DNA sequence encoding at least a portion of an autoantigen, transplant antigen, etc. In response to this vaccination, a suppressive response is evoked. Antigen-specific T cell proliferation is inhibited and Th1 cytokine production is reduced.

The prevention of autoimmune disease involving the targeted antigen, is accomplished by administration of the vaccine prior to development of overt disease. The treatment of ongoing disease, where the suppressive vaccination stabilizes or improves the clinical symptoms of the patient, is of particular interest. Such treatment is desirably performed prior to complete loss of function in the affected tissues.

A DNA expression cassette encoding all, substantially all, or a portion of an antigen, encoding at least one complete epitope, usually as part of a vector, is introduced into tissue of the recipient. The gene, or minigene, is expressed in the tissue, and the encoded polypeptide acts as an immunogen, or antigen. It may be hypothesized that the presentation of the antigen sequence by a "non-professional" cell, lacking co-stimulatory molecules such as CD80 and CD86, stimulates a suppressive T cell response.

The DNA expression cassette will comprise most or all of the sequence encoding an antigen fragment. The coding sequence may be truncated at the 5' or 3' terminus and may be a fragment of the complete polypeptide sequence. In one embodiment of the invention, the sequence encodes a peptide fragment that is known to be presented to pathogenic T cells, for example peptides presented by Class II MHC molecules of the host. Such peptides have been described in the literature, and are typically of about 8 to about 30 amino acids in length. In another embodiment, the sequence encodes the complete antigenic protein, or substantially all of the antigenic protein. In yet another embodiment, the sequence encodes a self protein in which portions of the self protein that may be deleterious if injected, or that may reduce the effectiveness of the tolerizing regimen, are removed.

The vaccine may be formulated with one epitope or a cocktail of epitope sequences. It may be desirable in some cases to include multiple sequences, where each encodes a different epitope. For example, see Leadbetter et al. (1998) J. Immunol. 161:504-512. A formulation comprised of multiple coding sequences of distinct epitopes may be used to induce a more potent and/or sustained suppressive response. By specifically targeting multiple autoreactive T cell populations, such a formulation may slow or prevent the development of autoantigen resistance.

In addition to the specific epitopes and polypeptides of autoantigens, the immune response may be enhanced by the inclusion of CpG sequences, as described by Krieg et al. (1998) *Trends Microbiol.* 6:23-27, and helper sequence, King et al. (1998) *Nat. Med.* 4:1281-1286. Biological effects of DNA motifs like unmethylated CpG dinucleotides, in particular base contexts (CpG-S motifs), may modulate innate immune responses when injected into animals.

The antigen sequences are inserted into an appropriate expression cassette. The expression construct is prepared in conventional ways. The cassette will have the appropriate transcriptional and translational regulatory sequences for expression of the sequence in the recipient cells. The cassette will generally be a part of a vector, which contains a suitable origin of replication, and such genes encoding selectable markers as may be required for growth, amplification and manipulation of the vector, prior to its introduction into the recipient. Suitable vectors include plasmids, YACs, BACs, bacteriophage, retrovirus, adenovirus, and the like. Conveniently, the expression vector will be a plasmid. Prior to introduction into the recipient, the cassette may be isolated from vector sequences by cleavage, amplification, etc. as known in the art. For injection, the DNA may be supercoiled or linear, preferably supercoiled. The cassette may be maintained in the host cell for extended periods of time, or may be transient, generally transient. Stable maintenance is achieved by the inclusion of sequences that provide for integration and/or maintenance, e.g. retroviral vectors, EBV vectors and the like.

The expression cassette will generally employ an exogenous transcriptional initiation region, i.e. a promoter other than the promoter which is associated with the T cell receptor in the normally occurring chromosome. The promoter is functional in host cells, particularly host cells targeted by the cassette. The promoter may be introduced by recombinant methods in vitro, or as the result of homologous integration of the sequence by a suitable host cell. The promoter is operably linked to the coding sequence of the antigen to produce a translatable mRNA transcript. Expression vectors conveniently will have restriction sites located near the promoter sequence to facilitate the insertion of antigen sequences.

Expression cassettes are prepared comprising a transcription initiation region, which may be constitutive or inducible, the gene encoding the antigen sequence, and a transcriptional termination region. The expression cassettes may be introduced into a variety of vectors. Promoters of interest may be inducible or constitutive, usually constitutive, and will provide for transcription in the recipient cells. The promoter may be active only in the recipient cell type, or may be broadly active in many different cell types. Many strong promoters for mammalian cells are known in the art, including the β-actin promoter, SV40 early and late promoters, immunoglobulin promoter, human cytomegalovirus promoter, retroviral LTRs, etc. The promoters may or may not be associated with enhancers, where the enhancers may be naturally associated with the particular promoter or associated with a different promoter.

A termination region is provided 3' to the coding region, where the termination region may be naturally associated with the variable region domain or may be derived from a different source. A wide variety of termination regions may be employed without adversely affecting expression.

A small number of nucleotides may be inserted at the terminus of the autoantigen sequence, usually not more than 20, more usually not more than 15. The deletion or insertion of nucleotides will usually be as a result of the needs of the construction, providing for convenient restriction sites, addition of processing signals, addition of a consensus Kozak sequence, ease of manipulation, improvement in levels of expression, or the like. In addition, one may wish to substitute one or more amino acids with a different amino acid for similar reasons, usually not substituting more than about five amino acids in the region.

The DNA vectors are suspended in a physiologically acceptable buffer, generally an aqueous solution e.g. normal saline, phosphate buffered saline, water, etc. Stabilizing agents, wetting and emulsifying agents, salts for varying the osmotic pressure or buffers for securing an adequate pH value, and skin penetration enhancers can be used as auxiliary agents. The DNA will usually be present at a concentration of at least about 1 ng/ml and not more than about 10 mg/ml, usually at about from 100 μg to 1 mg/ml.

The DNA tolerizing therapeutic may be fractionated into two or more doses, of at least about 1 μg, more usually at least about 100 μg, and preferably at least about 1 mg per dose, administered from about 4 days to one week apart. In some embodiments of the invention, the individual is subject to a series of vaccinations to produce a full, broad immune response. According to this method, at least two and preferably four injections are given over a period of time. The period of time between injections may include from 24 hours apart to two weeks or longer between injections, preferably one week apart. Alternatively, at least two and up to four separate injections are given simultaneously at different parts of the body.

The DNA therapeutic is injected into muscle or other tissue subcutaneously, intradermally, intravenously, orally or directly into the spinal or synovial fluid. Of particular interest is injection into skeletal muscle. The genetic therapeutic may be administered directly into the individual to be immunized or ex vivo into removed cells of the individual which are reimplanted after administration. By either route, the genetic material is introduced into cells which are present in the body of the individual. Alternatively, the genetic therapeutic may be introduced by various means into cells that are removed from the individual. Such means include, for example, transfection, electroporation and microprojectile bombardment. After the genetic construct is taken up by the cells, they are reimplanted into the individual. Otherwise non-immunogenic cells that have genetic constructs incorporated therein can be taken from one individual and implanted into another.

Bupivacaine or compounds having a functional similarity may be administered prior to or contemporaneously with the vaccine. Bupivacaine is a homologue of mepivacaine and related to lidocaine. It renders muscle tissue voltage sensitive to sodium challenge and effects ion concentration within the cells. In addition to bupivacaine, mepivacaine, lidocaine and other similarly acting compounds, other contemplated cell stimulating agents include lectins, growth factors, cytokines and lymphokines such as platelet derived growth factor (PDGF), gCSF, gMCSF, epidermal growth factor (EGF) and IL-4.

As an alternative, or in addition to DNA tolerization, specific peptides, altered peptides, or proteins may be administered therapeutically to induce antigen-specific tolerance to treat autoimmunity. Native peptides targeted by the autoimmune response can be delivered to induce antigen-specific tolerance (Science 258:1491-4). Native peptides have been delivered intravenously to induce immune tolerance (J Neurol Sci. 152:31-8).

Delivery of peptides that are altered from the native peptide, is also known in the art. Alteration of native peptides with selective changes of crucial residues (altered peptide ligands or "APL") can induce unresponsiveness or change the responsiveness of antigen-specific autoreactive T cells.

"Peptide analogs" are at least seven amino acids in length and contain at least one difference in amino acid sequence between the analog and native antigenic peptide. An L-amino acid from the native peptide may be altered to any other one of the 20 L-amino acids commonly found in proteins, any one of the corresponding D-amino acids, rare amino acids, such as 4-hydroxyproline, and hydroxylysine, or a non-protein amino acid, such as β-alanine and homoserine. Also included with the scope of the present invention are amino acids that have been altered by chemical means such as methylation (e.g., α-methylvaline), amidation of the C-terminal amino acid by an alkylamine such as ethylamine, ethanolamine, and ethylene diamine, and acylation or methylation of an amino acid side chain function (e.g., acylation of the epsilon amino group of lysine), deimination of arginine to citrulline, isoaspartylation, or phosphorylation on serine, threonine, tyrosine or histidine residues.

The mechanism of action of how altered peptide ligands are efficacious may involve incomplete mobilization of the T cell receptor (TCR). There are several possible functional alterations that the APL can induce and these include: Simple antagonist, where the APL may compete for MHC binding with the native peptide on the antigen presenting cell and not allow for complete T cell activation. This implies that there is no signal transmitted through the T cell receptor by the APL. Anergy, where the APL induces a state of complete nonresponsiveness in the T cell such that the T cell does not respond to the native peptide. Phenotypic switching, where the APL may induce a functional switch in the T cell such that it decreases the production of proinflammatory cytokines and/or increase the production of noninflammatory cytokines such as IL-4 or IL-10.

Peptides and peptide analogs may be synthesized by standard chemistry techniques, including synthesis by automated procedure. In general, peptide analogs are prepared by solid-phase peptide synthesis methodology which involves coupling each protected amino acid residue to a resin support, preferably a 4-methylbenzhydrylamine resin, by activation with dicyclohexylcarbodiimide to yield a peptide with a C-terminal amide. Alternatively, a chloromethyl resin (Merrifield resin) may be used to yield a peptide with a free carboxylic acid at the C-terminus. After the last residue has been attached, the protected peptide-resin is treated with hydrogen fluoride to cleave the peptide from the resin, as well as deprotect the side chain functional groups. Crude product can be further purified by gel filtration, HPLC, partition chromatography, or ion-exchange chromatography.

Candidate peptide analogs may be screened for their ability to treat disease by an assay measuring competitive binding to MHC, and an assay measuring T cell proliferation. Those analogs that inhibit binding of the native peptides and do not stimulate proliferation of auto-reactive T cells are useful therapeutics. Candidate peptide analogs are further tested for their property of stimulating or inhibiting proliferation of T cells, by measuring the ability of the analog to cause proliferation of T cells in a direct fashion, or measuring the ability of the peptide analog to inhibit proliferation of T cells induced by a native peptide.

The peptides are administered to the patient as one or a cocktail of different epitopes, through a route, for example intravenous or subcutaneous, that provides for suppression of the immune response. APL and native peptides have been delivered both IV and subcutaneously in doses of 0.5-100 mg/dose on a bi-weekly to monthly basis.

In another embodiment, whole protein antigens targeted by the autoimmune response can be delivered to restore immune tolerance to treat autoimmunity (Science 263:1139).

Allergen immunotherapy, or hyposensitization is the parenteral administration of allergenic extracts as antigens at periodic intervals, usually on an increasing dosage scale to a dosage that is maintained as maintenance therapy. Indications for immunotherapy are determined by diagnosis of antibody specificity as described above. Allergen immunotherapy is performed by providing injections of the allergen to the allergic subject on a regular basis, with the goal of reducing the symptoms and signs of an allergic reaction or prevention of future anaphylaxis against antigens such as insect venom, penicillin, etc. This is usually done initially with low doses, with gradual dosage increases over a period of weeks.

Immunotherapy is specific to the allergen injected. It results in the following immunologic changes: a shift in T cell response from a Th2-type response to a Th1-type response with corresponding changes in cytokine production, decreased allergen-specific IgE production, increased allergen-specific IgG production, decreased inflammatory cells, decreased mediators of inflammation and decreased histamine-releasing factors. These changes result in decreased reactivity to the allergen in the target organ.

The amount of allergen to be injected may be empirically derived, and will depend on the size of the recipient, usually at least about 100 ng allergen/kilogram of body weight, and not more than about 1 mg allergen/kilogram body weight. Frequently the dose will be increased through the course of injections by as much as about ten to one million fold. Injection schedules vary with individual patients. For example, Allpyral preparations are administered every 1-2 weeks until a maintenance dose is reached. Maintenance injections are administered every 2-4 weeks. It should be re-emphasized that immunotherapy schedules are individualized and fixed schedules are not recommended. Allergy injections rarely go on "forever" but can usually be stopped after a patient has experienced no allergic symptoms and has required no medication for 18-24 consecutive months while on the maintenance schedule. Duration of treatment for the average patient is 3 to 5 years but could be longer in certain clinical settings. If symptoms recur after a 6 to 12 months observation period following discontinuation of immunotherapy, re-evaluation is warranted.

Allergen immunotherapy is appropriate for the following indications: Severe, seasonal (lasting 2 or more years) or perennial, IgE-dependent allergic rhinoconjunctivitis in which optimal allergen avoidance and medication have not been sufficiently effective in controlling symptoms. IgE-mediated allergic asthma; particularly where there is a clear temporal association between exposure to the allergen and signs and symptoms of asthma, and those in which symptoms have occurred during two or more allergy seasons in successive years. IgE-mediated asthma caused by house dust mites or ragweed pollen may be treated with allergen immunotherapy. IgE-mediated anaphylactic reactions to insect stings. Immunotherapy with venom from yellow jackets, yellow hornets, white-faced hornets, wasps and honey-bees, and with whole-body extracts of fire-ants, is effective.

Tissue Transplant Rejection Immune rejection of tissue transplants, including lung, heart, liver, kidney, pancreas, and other organs and tissues, is mediated by immune responses in the transplant recipient directed against the transplanted organ. Allogeneic transplanted organs contain proteins with variations in their amino acid sequences when compared to the amino acid sequences of the transplant recipient. Because the amino acid sequences of the transplanted organ differ from those of the transplant recipient they frequently elicit an immune response in the recipient against the transplanted organ. Rejection of transplanted organs is a major complication and limitation of tissue transplant, and can cause failure of the transplanted organ in the recipient. The chronic inflammation that results from rejection frequently leads to dysfunction in the transplanted organ. Transplant recipients are currently treated with a variety of immunosuppressive agents to prevent and suppress rejection. These agents include glucocorticoids, cyclosporin A, Cellcept, FK-506, and OKT3.

It is to be understood that this invention is not limited to the particular methodology, protocols, cell lines, animal species or genera, and reagents described, as such may vary. It is also to be understood that the terminology used herein is for the purpose of describing particular embodiments only, and is not intended to limit the scope of the present invention which will be limited only by the appended claims.

As used herein the singular forms "a", "and", and "the" include plural referents unless the context clearly dictates otherwise. All technical and scientific terms used herein have the same meaning as commonly understood to one of ordinary skill in the art to which this invention belongs unless clearly indicated otherwise.

The following examples are put forth so as to provide those of ordinary skill in the art with a complete disclosure and description of how to make and use the subject invention, and are not intended to limit the scope of what is regarded as the invention. Efforts have been made to ensure accuracy with respect to the numbers used (e.g. amounts, temperature, concentrations, etc.) but some experimental errors and deviations should be allowed for. Unless otherwise indicated, parts are parts by weight, molecular weight is average molecular weight, temperature is in degrees centigrade; and pressure is at or near atmospheric.

All publications and patent applications cited in this specification are herein incorporated by reference as if each individual publication or patent application were specifically and individually indicated to be incorporated by reference.

EXPERIMENTAL

Example 1

Antigen Array Characterization of the Specificity of the Autoantibody Response in EAE in Rats and Mice To determine the autoantibody specificity profile in the serum of animals with EAE, an assay was performed testing the binding of serum antibodies to a protein microarray.

Antigen arrays were generated by spotting the immunodominant myelin peptide epitopes and purified native myelin basic protein, as listed in Table 1. FIGS. 1A-D are scanned imaged of arrays probed with serum from a normal control rat (A) and 3 Lewis rats induced to develop EAE with different myelin protein peptides in complete Freund's adjuvant (B-D), followed by Cy-3 labeled anti-rat Ig secondary antibody.

Quantitative computer analysis of the scanned images is presented in Table 1. The reported numbers represent the ratio of the fluorescence intensity of antigens recognized by serum derived from animals with EAE relative to control serum adjusting for background levels such that ratios greater or less than 1 (1= no difference) represent a statistically significant difference with a >95% confidence interval. Results were confirmed by ELISA. These results demonstrate that antigen arrays powerfully identify the peptide-specificity of the autoantibody response in EAE.

TABLE 1

Antigen array characterization of the specificity of the autoantibody response in EAE in lewis rats.

|  | Rat EAE-1 MBP 68-86 | Rat EAE-2 PLP 139-151 | Rat EAE-3 MOG 35-55 |
|---|---|---|---|
| MBP 68-86 | 117.7 | 1.0 | 1.0 |
| PLP 139-151 | 1.0 | 67.6 | 1.0 |
| GP MBP | 25.4 | 1.0 | 1.0 |
| MOG 35-55 | 1.0 | 1.0 | 15.6 |
| MBP Ac 1-11 | 1.0 | 4.0 | 1.0 |
| Green/Red | 2.3 | 0.8 | 2.1 |
| Green | 1.8 | 0.7 | 2.5 |
| alkaline phosphatase | 1.0 | 1.0 | 1.0 |
| influenza A/B | 1.0 | 1.0 | 1.0 |
| BSA | 1.0 | 1.0 | 1.0 |
| blank | 1.0 | 1.0 | 1.0 |
| flag | 1.0 | 1.0 | 1.0 |
| Control pep-127 | 1.0 | 1.0 | 1.0 |
| Control pep-128 | 1.0 | 1.0 | 1.0 |
| Control pep-129 | 1.0 | 1.0 | 1.0 |
| Control pep-130 | 1.0 | 1.0 | 1.0 |
| Control pep-131 | 1.0 | 1.0 | 1.0 |

Example 2

Figure 1:
FIGS. 1A to 1D shows an antibody specificity profile including an antigen array characterization (antigen array profile) of the myelin peptide-specificity of the autoantibody response in EAE in rats. Antigen arrays were generated by spotting the immunodominant myelin peptide epitopes and purified native myelin basic protein (listed in Table 1). A-D represent scanned imaged of arrays probed with serum from a normal control rat (A) and 3 Lewis rats induced to develop EAE with different myelin protein peptides in complete Freund's adjuvant (B-D), followed by Cy-3 labeled anti-rat Ig secondary antibody. Results were confirmed by ELISA. Quantitative computer analysis of the scanned images is presented in Table 1. The reported numbers represent the ratio of the fluorescence intensity of antigens recognized by SLE relative to control serum adjusting for background levels such that ratios greater or less than 1 (1=no difference) represent a statistically significant difference with a >95% confidence interval. Antigen arrays powerfully identify the peptide-specificity of the autoantibody response in EAE.
Figure 1:
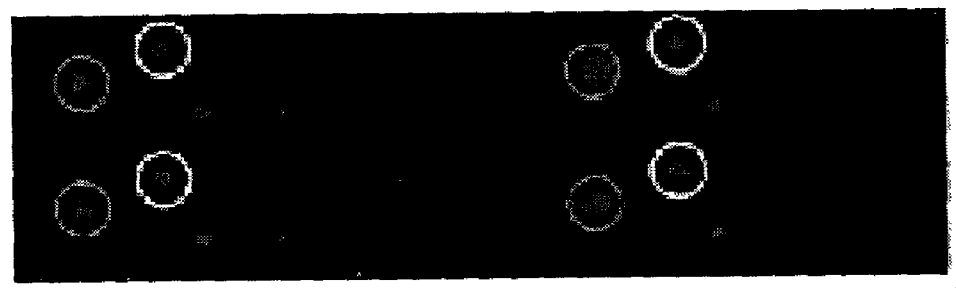
Figure 1:
Figure 1:
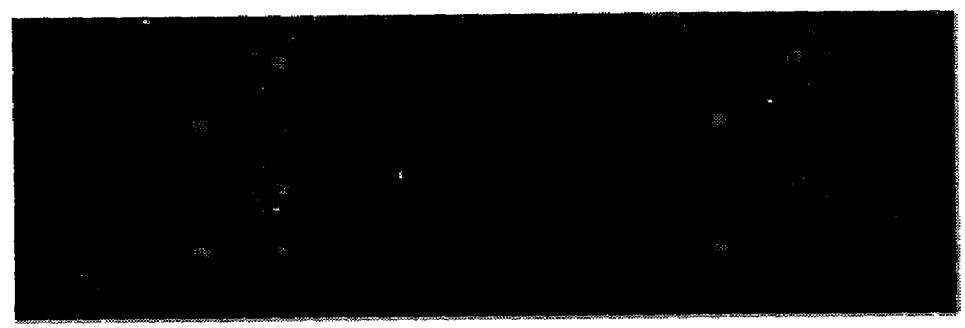
Figure 2:
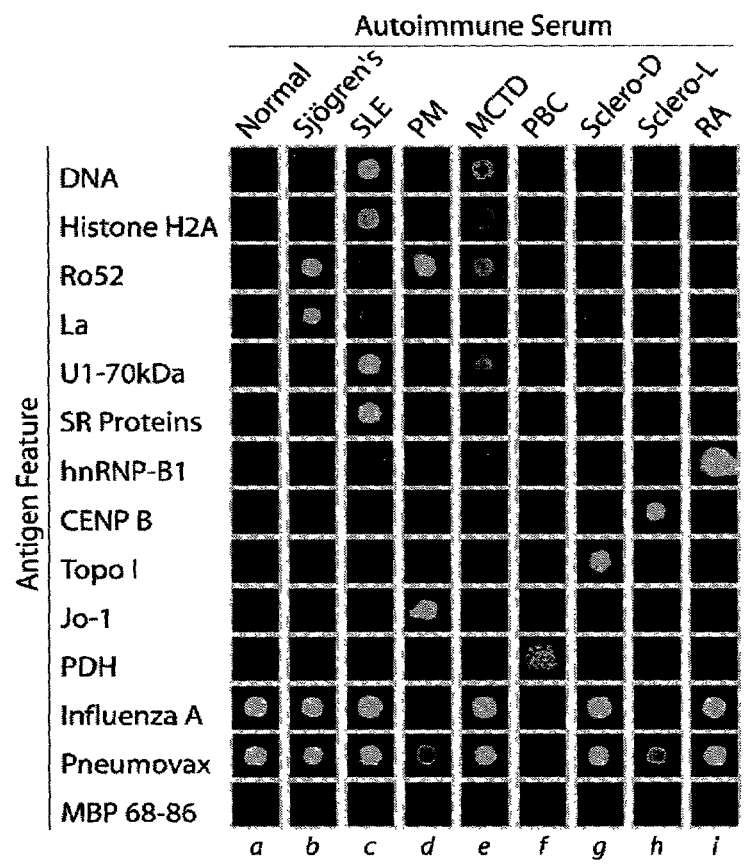
FIG. 2 shows an antibody specificity profile including an antigen array identification and characterization (antigen array profile) of the autoantibody specificity in 8 different human autoimmune diseases. Ordered autoantigen arrays were generated by spotting 192 distinct putative autoantigens in quadruplicate sets using a robotic microarrayer to create a 1152-feature rheumatic disease autoantigen array. Spotted antigens include: 36 recombinant or purified proteins including Ro52, La, histidyl-tRNA synthetase (Jo-1), SR proteins, histone H2A (H2A), Sm-B/B', the 70 kDa and C component of the U1 small nuclear ribonucleoprotein complex (U1-70 kDa, U1snRNP-C), Sm-B/B', hnRNP-B1, Sm/RNP complex, topoisomerase I (topo I), centromere protein B (CENP B), and pyruvate dehydrogenase (PDH); six nucleic acid-based putative antigens including several forms of mammalian double-stranded DNA (dsDNA) and synthetic single-stranded DNA (ssDNA); and 154 peptides representing snRNP proteins, Sm proteins, and histones H1, H2A, H3 and H4. In addition, we spotted antibodies specific for human IgG and IgM (α-IgG and α-IgM); the vaccines for influenza A and pneumococcus (Pneumovax); and a mixture of antibodies pre-labeled with Cy-3- and Cy-5 to serve as marker spots to orient the arrays (the yellow features). Autoantigen arrays were incubated with diluted patient serum samples from (a) a healthy individual (normal) for which no specific autoantibody reactivities were detected; (b) Sjögren's syndrome demonstrating autoantibody reactivity against Ro52 and La; (c) SLE demonstrating reactivity against DNA, histone H2A, U1-70 kDa, and SR protein; (d) PM demonstrating reactivity against Jo-1 and Ro52; (e) MCTD demonstrating reactivity against DNA, histone H2A, Ro52, and U1-70 kDa; (f) PBC demonstrated reactivity against PDH; (g) sclero-D demonstrating reactivity against topo I; (h) sclero-L demonstrating reactivity against CENP B; and (i) RA demonstrating reactivity against hnRNP-B1. The autoimmune disease serum used to probe each array is indicated along the top of the figure, and each column of cut and pasted antigen features contained within a gray box are representative antigen features from a single array. A myelin basic protein peptide recognized on arrays by autoantibodies in serum from rodents with experimental autoimmune encephalomyelitis was included as a representative negative control (MBP 68-86).

Determination of the Patient Antibody Specificity Profile in Autoimmune Rheumatic Diseases Autoantigen arrays identify autoantibody profiles characteristic of eight distinct human autoimmune rheumatic diseases. Representative examples of autoantigen array analysis of over 50 highly-characterized autoimmune serum samples are presented (FIG. 2).

Ordered autoantigen arrays were generated by spotting 192 distinct putative autoantigens in quadruplicate sets using a robotic microarrayer to create a 1152-feature rheumatic disease autoantigen array. Spotted antigens include: 36 recombinant or purified proteins including Ro52, La, histidyl-tRNA synthetase (Jo-1), SR proteins, histone H2A (H2A), Sm-B/B', the 70 kDa and C component of the U1 small nuclear ribonucleoprotein complex (U1-70 kDa, U1snRNP-C), Sm-B/B', hnRNP-B1, Sm/RNP complex, topoisomerase I (topo I), centromere protein B (CENP B), and pyruvate dehydrogenase (PDH); six nucleic acid-based putative antigens including several forms of mammalian double-stranded DNA (dsDNA) and synthetic single-stranded DNA (ssDNA); and 154 peptides representing snRNP proteins, Sm proteins, and histones H1, H2A, H3 and H4. In addition, we spotted antibodies specific for human IgG and IgM (α-IgG and α-IgM); the vaccines for influenza A and pneumococcus (Pneumovax); and a mixture of antibodies pre-labeled with Cy-3- and Cy-5 to serve as marker spots to orient the arrays (the yellow features). Autoantigen arrays were incubated with diluted patient serum samples from (a) a healthy individual (normal) for which no specific autoantibody reactivities were detected; (b) Sjögren's syndrome demonstrating autoantibody reactivity against Ro52 and La; (c) SLE demonstrating reactivity against DNA, histone H2A, U1-70 kDa, and SR protein; (d) PM demonstrating reactivity against Jo-1 and Ro52; (e) MCTD demonstrating reactivity against DNA, histone H2A, Ro52, and U1-70 kDa; (f) PBC demonstrated reactivity against PDH; (g) sclero-D demonstrating reactivity against topo I; (h) sclero-L demonstrating reactivity against CENP B; and (i) RA demonstrating reactivity against hnRNP-B1. The autoimmune disease serum used to probe each array is indicated along the top of the figure, and each column of cut and pasted antigen features contained within a gray box are representative antigen features from a single array. A myelin basic protein peptide recognized on arrays by autoantibodies in serum from rodents with experimental autoimmune encephalomyelitis was included as a representative negative control (MBP 68-86). Bound antibodies were detected using Cy-3-conjugated goat-anti-human IgM/IgG prior to scanning.

Shown are published, highly characterized serum samples derived from patients with Sjögren's syndrome, SLE, PM, mixed connective tissue disease (MCTD), PBC, diffuse and limited scleroderma (sclero-D and sclero-L), and rheumatoid arthritis (RA), identifying distinct and diagnostic autoantibody specificity patterns. For example, SLE-specific autoantibodies directed against DNA and histone were detected (FIG. 2c). DNA-specific autoantibodies are pathogenic in some models, and their titers frequently correlate with disease activity. Jo-1 autoantibodies (FIG. 2d frequently predate clinical PM by months to years, and predict development of interstitial lung disease and a poor prognosis. Autoantibodies derived from patients with either diffuse or limited scleroderma uniquely target topo I and CENP B, respectively (FIG. 2g and h). CENP B autoantibodies are associated with a low incidence of interstitial pulmonary and renal disease, while the presence of topoisomerase autoantibodies correlates with heightened risk of pulmonary fibrosis and reduced survival. Autoantigen reactivity was not observed when sera from 10 healthy individuals were employed as probes, despite reproducible detection of antibodies to pneumococcus and influenza (FIG. 2a). These array profiles correlated precisely with previously described results of conventional assays.

These results demonstrate that antigen arrays detect autoantibodies specific for proteins, peptides, nucleic acids, posttranslationally modified antigens, and protein complexes. Such information can be used for diagnosis, prognostication, monitoring response to therapy, and to develop and select antigen-specific therapies.

Example 3

Determination of the Autoantibody Specificity Profile from the Cerebral Spinal Fluid from Human Multiple Sclerosis Patients Antigen arrays containing myelin proteins and peptides were used to characterize the specificity of the autoantibody response in cerebral spinal fluid samples derived from human patients with multiple sclerosis (FIG. 3). The arrays in FIG. 3 demonstrate detection of cerebral spinal fluid autoantibodies specific for whole myelin basic protein (MBP), MBP peptide 1-20 (corresponding to amino acids 1-20 of MBP), MBP peptide 68-86, whole myelin oligodendrocyte protein (MOG), MOG peptide 35-55, and proteolipid protein (PLP) peptide 139-151. As in Example 2, such information can be used for diagnosis and to develop, monitor and select specific therapy.

2400-spot 'myelin proteome' arrays were produced by spotting these putative myelin antigens using a robotic microarrayer, probed with cerebral spinal fluid followed by Cy-3-labeled anti-human Ig secondary antibody, scanned using a GenePix scanner, and images analyzed using GenePix software to determine levels of autoantibody binding to each spot. These arrays contain 400 different myelin protein and peptide epitopes including MBP, proteolipid protein (PLP), myelin oligodendrocyte protein (MOG), overlapping peptides representing these proteins, and peptides representing dominant epitopes from additional myelin autoantigens including cyclic nucleotide phosphodiesterase (CNPase), myelin-associated glycoprotein (MAG), and myelin-associated oligodendrocytic basic protein (MBOP).

In the control patient, although antibodies specific for common and ubiquitous human pathogens including influenza virus and Streptococcus pneumonia are detected, no antibodies specific for myelin proteins and peptides are detected. In MS patient 1, antigen arrays detect autoantibodies specific for whole myelin basic protein (MBP), whole myelin oligodendrocyte protein (MOG), as well as autoantibodies recognizing MOG peptide 35-55, MBP peptide 1-20, and MBP peptide 68-86. In contrast, in MS patient 2 autoantibodies are detected against MOG protein and MOG peptide 25-42. In MS patient 3, autoantibodies specific for proteolipid protein (PLP) peptide 139-151 are identified.

Example 4

Figure 5:
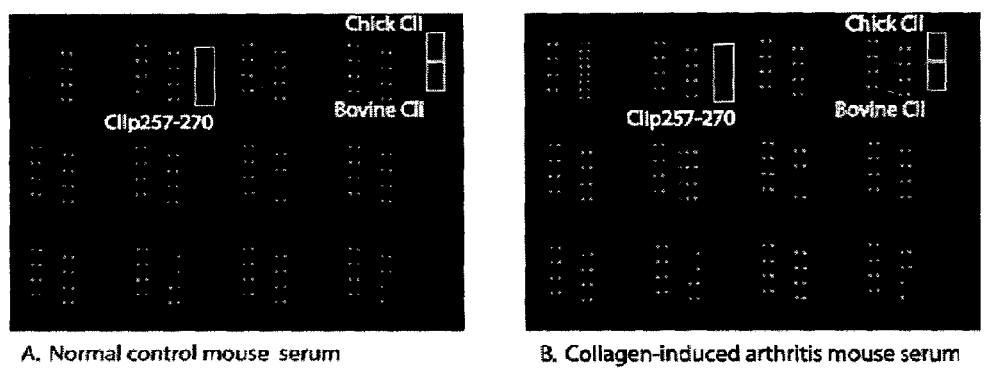

Use of Patient Autoantibody Specificity Profiles to Guide Selection of Antigen Specific Therapies to Treat Rheumatoid Arthritis Antigen array analysis of the autoantibody response in an animal model for rheumatoid arthritis, collagen-induced arthritis (CIA). FIG. 5 presents images of the RA/CIA array containing approximately 450 different synovial joint proteins and peptides, including type II collagen (CII), collagen types I, III, IV, V, IX, and XI, GP-39, immunoglobulin, Sa, calpastatin, RA33, Aldolase A, heat shock protein-60 and -65, glucose-6-phosphate isomerase, the molecular chaperone BiP, and citrulline-modified fibrin and filaggrin peptides and proteins.

FIG. 5 shows an antibody specificity profile using an array of antigens and epitopes derived from synovial joints to determine the specificity of the autoantibody response in CIA. 2000-spot 'synovial proteome' arrays were produced by spotting putative synovial joint antigens using a robotic microarrayer, probed with CIA mouse serum followed by Cy-3-labeled anti-mouse Ig secondary antibody, scanned using a GenePix scanner, and images analyzed using GenePix software to determine levels of autoantibody binding to each spot. A-B represent scanned images of arrays probed with serum from a control DBA/1 LacJ mouse (A) and a DBA/1LacJ mouse with CIA (B). Autoantibody reactivity against type II collagen and the immunodominant type II collagen peptide 257-270 is observed. Results were confirmed by ELISA and are representative of autoantibody reactivity observed in additional mice. For the purposes of diagnosis and treatment determination of the specificity of the autoantibody response can also be accomplished using conventional methods including radioimmunoassays, enzyme-linked immunosorbent assays (ELISA), fluorescent-based autoantibody tests, and/or Western blot analysis.

Treatment of CIA with antigen-specific tolerizing DNA treatment encoding the antigen array identified targets of the autoantibody response in CIA. A DNA tolerizing treatment was designed based on the epitope specificity profile determined in FIG. 5 according to this invention. CIA was prevented or treated using the DNA tolerizing treatment encoding the epitope of type II collagen (CII), CIIp257-270, identified as being targeted by the autoantibody response using antigen arrays as demonstrated in FIG. 5. Additionally, tolerizing DNA encoding whole type II collagen, which is also identified as a target of the autoimmune response in CIA using antigen arrays as demonstrated in FIG. 5, also effectively prevented and treated CIA. Table 5 presents data from a representative experiment.

TABLE 5

| Tolerizing DNA Treatment Group | Incidence of CIA | Net CIA Score |
|---|---|---|
| pTarget (DNA vector only, control) | 0.53 | 22 |
| ptarget + IL-4 (DNA vector plus IL-4, control) | 0.4 | 32 |
| Minigene (DNA encoding CIIp257-270) | 0.13 | 4 |
| Minigene + IL-4 | 0 | 4 |

TABLE 5-continued

| Tolerizing DNA Treatment Group | Incidence of CIA | Net CIA Score |
|---|---|---|
| CII (DNA encoding whole CII) | 0.13 | 8 |
| CII + IL-4 | 0.06 | 4 |

The DNA encoding type II collagen (CII) was administered to DBA/1LacJ mice intramuscularly on a once per week basis at a dose of 100 µg of each DNA plasmid twice before induction of CIA with CII emulsified in Complete Fruend's Adjuvant. Animals were boosted with CII in Incomplete Fruend's Adjuvant at day 20. Each mouse was scored daily for arthritis using the visual scoring system.

Example 5

Figure 4:
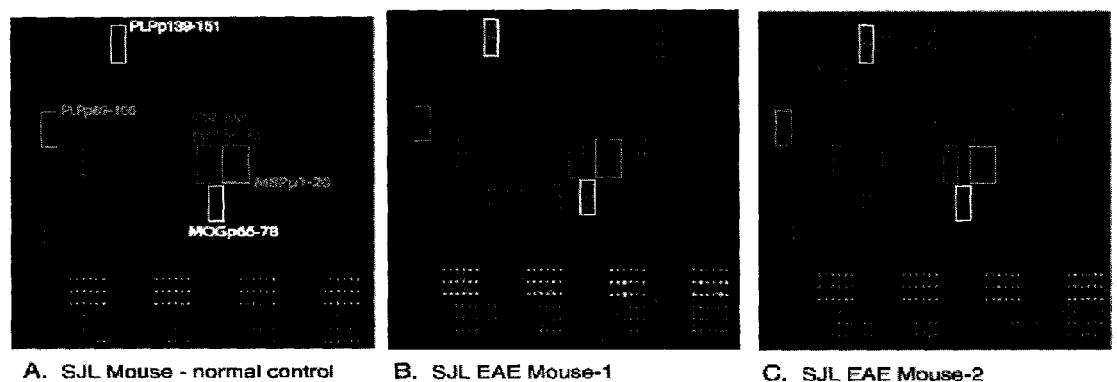

Use of Antibody Specificity Profiles to Guide Development and Selection of Antigen Specific Therapies to Treat Multiple Sclerosis Antigen array analysis of the autoantibody response in an animal model for multiple sclerosis, EAE. FIG. 4 presents images of the 2400-spot MS/EAE array containing approximately 400 different myelin protein and peptide epitopes including MBP, proteolipid protein (PLP), myelin oligodendrocyte protein (MOG), overlapping peptides representing these proteins, and peptides representing dominant epitopes from additional myelin autoantigens including cyclic nucleotide phosphodiesterase (CNPase), myelin-associated glycoprotein (MAG), and myelin-associated oligodendrocytic basic protein (MBOP).

FIG. 4 demonstrates use of this array containing a spectrum of myelin antigens and epitopes to study the specificity of the autoantibody response in EAE. 2400-spot 'myelin proteome' arrays were produced by spotting putative myelin antigens using a robotic microarrayer, probed with EAE mouse serum followed by Cy-3-labeled anti-mouse Ig secondary antibody, scanned using a GenePix scanner, and images analyzed using GenePix software to determine levels of autoantibody binding to each spot. A-C represent scanned images of arrays probed with serum from a control mouse (A) and 2 SJL mice 87 days post-EAE induction with PLPp139-151 that developed relapsing disease (B&C). Autoantibody reactivity against the inducing peptide PLPp139-151 is significantly stronger in the 2 mice with EAE relative to the control, autoantibody reactivity against an adjacent intra-molecular epitope PLPp89-106 is observed in mouse-2 but not mouse-1 or the control, and autoantibody reactivity against inter-molecular proteins and epitopes including MOG protein, MOGp66-78, CNPase p343-373, and MBPp1-20 are observed in both mice with EAE but not the control. Results were confirmed by ELISA and are representative of autoantibody reactivity observed in additional mice.

SJL mice induced to develop EAE with PLPp139-151 in Complete Freund's Adjuvant (CFA) undergo intra- and inter-molecular spreading of their autoantibody response to adjacent epitopes on PLP, and to epitopes on 3 additional myelin proteins including MBP, MOG, and CNPase (FIGS. 4B and C). In SJL mice with EAE, mice with fewer clinical relapses have significantly less spreading of the autoantibody response (FIG. 5). This observation that increased epitope spreading of the autoantibody response to additional myelin antigens is associated with relapsing and more severe disease provides further evidence that autoantibody specificity profiling using antigen arrays can be used to predict clinical outcomes in individual animals. Side-by-side enzyme-linked immunosorbent assay (ELISA) analysis identified and confirmed the antigen array determined specificity of the autoantibody response. Spreading of the autoantibody response and its correlation with more severe disease in EAE, a T cell-mediated disease, has not been previously described and demonstrates diagnostic and prognostic utility of determination of autoantibody specificity profiles. For the purposes of diagnosis and treatment determination of autoantibody specificity profiles can also be accomplished using conventional methods including radioimmunoassays, enzyme-linked immunosorbent assays (ELISA), fluorescent-based autoantibody tests, and/or Western blot analysis.

Antigen-specific DNA tolerizing therapeutics as an example of antigen-specific therapies. Chronic relapsing EAE can be prevented and treated by introduction of DNA plasmid minigenes encoding epitopes of PLP (*J. Immunol* 162:3336-41; *Curr. Dir. Autoimmun.* 2:203-16; Table 2). DNA vaccines encoding several whole myelin proteins were even more effective at treating EAE (Tables 2 and 3). Delivery of DNA vaccines encoding both myelin antigens in combination with IL-4 further enhanced the protective effects (Table 3).

TABLE 2

Antigen-specific DNA tolerizing therapeutics encoding antigen identified using the antibody specificity profile to treat chronic relapsing EAE.

| DNA | n | mean relpase rate | p value compared to cocktail |
|---|---|---|---|
| vehicle | 17 | 2.94 | 0.0064 |
| vector only | 16 | 3.875 | <0.0001 |
| cocktail | 16 | 1.563 | |

[1]Mice that were administered cocktail therapy were treated intramuscularly on a once per week basis at a dose of 50 µg of each the four major myelin plasmids, MBP, MOG, MAG, and PLP. The cocktail consists of DNA encoding these four myelin antigens, Treatment was begun immediately after recovery from the initial acute onset of EAE. Sera were collected when the mice were sacrificed at day 87 and used on the myelin protein arrays. Each mouse was scored daily for and the mean number of exacerbations of clinical paralysis (relapses) over 87 days is presented for each group of mice. p value calculated using the Student's two-tailed unpaired t test.

TABLE 3

Antigen-specific DNA tolerizing therapeutics encoding antigen identified using the antibody specificity profile to treat chronic relapsing EAE, inclusion of a DNA plasmid encoding IL-4 potentiates this effect.

| DNA | n | mean relapse rate | p value compared to cocktail/IL-4 |
|---|---|---|---|
| vehicle | 20 | 2.45 | 0.0018 |
| IL4 | 14 | 2.93 | 0.0003 |
| PLP139-151/IL-4 | 17 | 1.94 | 0.0158 |
| cocktail | 18 | 1.44 | 0.1714 |
| cocktail/IL-4 | 17 | 0.941 | |

[1]Mice that were administered cocktail were treated intramuscularly on a once per week basis at a dose of 25 µg of each the four major myelin plasmids, MBP, MOG, MAG, and PLP. The cocktail consists of DNA encoding these four myelin antigens, All other DNA was given at a dose of 50 µg of plasmid per animal on a once weekly basis. Treatment was begun immediately after recovery from the initial acute onset of EAE. Each mouse was scored daily for and the mean number of exacerbations of clinical paralysis (relapses) over 81 days is presented for each group of mice. p value calculated using the Student's two-tailed unpaired t test.

Use of the specificity of the autoantibody response to selected antigen-specific tolerizing therapy for more efficacious treatment of EAE. We treated chronic relapsing EAE in SJL mice with DNA plasmids encoding various myelin antigens identified by the antigen array determined antibody specificity profile. Table 4 presents the culminated results from multiple experiments using antigen-specific DNA tolerizing therapeutics to: (1) prevent induction of EAE, and (2) to treat established EAE. Table 4 demonstrates that antigen-specific DNA plasmids encoding a greater number of the protein array identified autoantigens targeted by the autoimmune process have superior efficacy in treating EAE compared to plasmids only encoding one of the targeted autoantigens (or encoding non-targeted myelin proteins). Use of antigen-specific therapies developed and selected based on the antigen array determined antigen specificity profile results in more efficacious therapies.

TABLE 4

Cumulative Results for Prevention and Treatment of EAE with Antigen-Specific DNA Tolerizing Therapeutics.

| Tolerizing DNA Formulation | EAE Disease Reduction | |
|---|---|---|
| | Without IL-4 | With IL-4 |
| Vector alone | − | − |
| MOG | −/+ | ++ |
| PLPp139-151 | + | ++ |
| Cocktail: MBP, MOG, MAG, PLP | +++ | ++++ |

Example 6

Use of Antibody Specificity Profiles to Monitor Response to Therapy

Analysis of animals protected against or treated for EAE with DNA plasmids demonstrated reduced epitope spreading of the autoantibody response on protein array analysis (FIG. 6). Individual mice are listed on the X axis, and peptide and protein antigens present on the 'myelin proteome' array on the Y axis. Green indicates lack of reactivity, and red indicates autoantibody reactivity. The cluster analysis algorithm groups mice based on similarities in the antigen array determined specificity of their autoantibody responses. This image represents a small region of the overall cluster. Normal mice (NMS) cluster and the predominance of green indicates lack of autoantibody reactivity to the listed antigens. SJL mice with chronic relapsing EAE treated with control vector or buffer (B and C) cluster and have significant autoantibody reactivity, indicated by red, against various myelin antigens. This observed spreading of the autoantibody response in these mice correlates with their more severe disease course, with an average of 2.4-3.5 relapses over the 87 day period. The average number of clinical exacerbations of paralysis (relapses) are presented at the top of the figure by the numbers over the bars indicating the relevant group of mice. In contrast, mice treated with the myelin protein cocktail DNA tolerizing therapeutic (containing a large number of the antigen array identified targets of the autoimmune response, and demonstrating the greatest efficacy in treating EAE [Table 4]) cluster and have a significant reduction in the spreading of their autoantibody response as indicated by the increased green relative to the other groups. This reduction in spreading of the autoimmune response correlated with their less-severe clinical course with an average of 1.5 relapses over the 87 day period.

FIG. 6 presents cluster analysis of the antigen array results from mice with EAE treated with antigen-specific DNA tolerizing therapeutics. The myelin protein cocktail DNA tolerizing regimen encoding 4 of the myelin antigens identified by antigen arrays as targeted by the autoantibody response powerfully reduced B cell epitope spreading (FIG. 6). This correlated with its significant reduction of disease activity as measured by relapse rate (Tables 2 and 3, FIG. 6). Thus, antigen array-based autoantibody profiling, in addition to having utility in guiding the selection of antigen-specific therapy, can also be utilized to monitor responses to antigen specific therapy. Although not shown, isotype analysis of antibodies binding to individual antigen features on the array will allow even more detailed analysis and prediction of therapeutic response. For example, in human autoimmune disease therapeutic efficacy may be indicated by antigen array identification of a shift in the antibody isotype subclasses from the Th1 isotype subclasses IgG1 and IgG3 associated with tissue injury to the Th2 isotype subclasses IgG2 and IgG4 associated with protection against tissue injury in autoimmune disease. Use of the specificity of the autoantibody response to select antigen-specific therapy fundamentally treats the autoimmune process by suppressing the spreading of the autoimmune response and this correlates with reduction of disease activity.

Example 7

Patient Antibody Specificity Profile-Based Therapy for Tissue Transplant

A major limitation of tissue transplant is the rejection of tissue transplants by the recipient's immune system. Tissue transplants include transplant of blood and blood-derived cells, as well as transplant of solid organs including heart, lung, kidneys, liver and other organs. Immune rejection is mediated by the recipients' immune system which recognizes allelic variations in the tissue transplant proteins. Tissue transplant rejection is mediated by recipient immune responses against the MHC class I and II proteins in the tissue transplant, and against other histocompatibility and additional antigens with allelic variation in the tissue transplant as compared to the recipient. When the transplant recipient's immune system reacts against the transplant it produces antibodies that bind antigens within the transplant.

Using tissue transplants between Balb/c ($H-2^d$) and Balb/k ($H-2^k$) mice, antigen arrays containing antigens and epitopes representing the $H-2^d$ class I and Class II MHC molecules are used to determine antibody profiles. Using standard protocols, hearts are transplanted from $H-2^d$ mice into ectopic abdominal locations in $H-2^k$ mice (ectopic transplantation enables close monitoring of the transplanted heart by simple palpation). Serum derived from recipient mice are analyzed using the described antigen arrays to identify antibody reactivity against the donor MHC molecules. Identification of antibody profiles enables identification of recipient animals rejecting the transplanted heart. Antibody profiles also enable assessment of the severity of rejection for prognostication, and guiding selection of non-specific therapy. Antibody specificity profiles can also be used to develop and select antigen-specific therapy to treat tissue transplant rejection to prevent demise of the transplanted tissue. In this example, graft survival is monitored by palpation of the transplanted heart.

Example 8

Antibody Specificity Profile-Based Therapy for Allergic Disease

Allergic diseases are mediated by aberrant immune responses directed against exogenous allergens to which a patient is exposed. Examples include allergic reactions to pollens, house dust mite antigens, bee venom, peanut oil, and other molecules existing in the environment. In allergic responses patients generate antibodies directed against the offending allergen(s). Arrays containing allergens, and immune epitopes representing allergens, are generated and used to determine a patient's profile of antibody specificities directed against allergens. Identification of a patient's antibody profile will facilitate diagnosis of the allergic disease and identification of the allergen against which the patient is reacting. The patient antibody specificity can be further used to develop and select the appropriate allergens to use to tolerize the patient. Tolerizing the patient involves administration of the offending allergen in a manner that turns off the patient's aberrant allergic immune response directed against it. The patient antibody specificity profile can also be used to monitor the patient's response to allergen tolerizing therapy, based on alterations in the anti-allergen antibody reactivity, titers of anti-allergen antibodies, and/or the isotype subclass use of anti-allergen antibodies.

What is claimed is:

1. A method for selecting an antigen-specific treatment regimen for a patient with multiple sclerosis comprising:
   (a) providing an autoantigen array comprising at least two autoantigen elements associated with multiple sclerosis wherein each autoantigen element further comprises at least one immunologic epitope(s);
   (b) physically contacting the autoantigen array from step (a) with a patient sample comprising antibodies from a patient having multiple sclerosis;
   (c) identifying the autoantigens associated with multiple sclerosis within the array that bind to antibodies within the patient sample from step (b);
   (d) comparing the antibodies from the patient sample bound to the autoantigens in step (c) with (1) antibodies from a positive reference or control sample wherein the antibodies from the positive reference or control sample are known to be associated with multiple sclerosis; and, (2) antibodies from a negative reference or control sample wherein the antibodies from the negative reference or control sample are not associated with multiple sclerosis, thereby determining an antibody specificity profile specific for the patient;
   (e) selecting an antigen-specific treatment regimen based on the antibody specificity profile; and
   (f) administering the antigen-specific treatment regimen, wherein the antigen-specific regimen comprises administering one or more autoantigens identified in step (c).

2. The method of claim 1 wherein the patient has not developed clinical symptoms.

3. The method of claim 1 wherein the patient has clinical symptoms.

4. The method of claim 1 wherein the autoantigen array comprises autoantigens selected from the group consisting of protein, polypeptide, peptide, DNA, RNA, lipid, glycosylated molecules, polypeptides with phosphorylation modifications, polypeptides with citrulline modifications, polysaccharides or other molecules.

5. The method of claim 1 wherein the autoantigen array is a microarray.

6. The method of claim 1 wherein the autoantigen array has addressable elements.

7. The method of claim 1 wherein the patient sample is a cerebrospinal sample.

8. The method of claim 1 wherein the antigen-specific treatment regimen comprises administering a protein, a peptide, or DNA encoding the protein or peptide.

9. The method of claim 1 wherein the autoantigens are selected from the group consisting of proteolipid protein (PLP); myelin basic protein (MBP); myelin oligodendrocyte protein (MOG); cyclic nucleotide phosphodiesterase (CNPase); myelin-associated glycoprotein (MAG), myelin-associated oligodendrocytic basic protein (MBOP); alpha-B-crystallin; viral and bacterial mimicry peptides; OSP (oligodendrocyte specific-protein); or citrulline-modified MBP.

10. A method for selecting an antigen-specific treatment regimen for a patient with rheumatoid arthritis comprising:
   (a) providing an autoantigen array comprising at least two autoantigen elements associated with rheumatoid arthritis wherein each autoantigen element further comprises at least one immunologic epitope(s);
   (b) physically contacting the autoantigen array from step (a) with a patient sample comprising antibodies from a patient having rheumatoid arthritis;
   (c) identifying the autoantigens associated with rheumatoid arthritis within the array that bind to antibodies within the patient sample from step (b);
   (d) comparing the antibodies from the patient sample bound to the autoantigens in step (c) with (1) antibodies from a positive reference or control sample wherein the antibodies from the positive reference or control sample are known to be associated with rheumatoid arthritis; and, (2) antibodies from a negative reference or control sample wherein the antibodies from the negative reference or control sample are not associated with rheumatoid arthritis, thereby determining an antibody specificity profile specific for the patient
   (e) selecting an antigen-specific treatment regimen based on the antibody specificity profile; and;
   (f) administering the antigen-specific treatment regimen, wherein the antigen-specific regimen comprises administering one or more autoantigens identified in step (c).

11. The method of claim 10 wherein the patient has not developed clinical symptoms.

12. The method of claim 10 wherein the patient has clinical symptoms.

13. The method of claim 10 wherein the autoantigen array comprises autoantigens selected from the group consisting of protein, polypeptide, peptide, DNA, RNA, lipid, glycosylated molecules, polypeptides with phosphorylation modifications, polypeptides with citrulline modifications, polysaccharides or other molecules.

14. The method of claim 10 wherein the autoantigen array is a microarray.

15. The method of claim 10 wherein the autoantigen array has addressable elements.

16. The method of claim 10 wherein the patient sample is a synovial sample.

17. The method of claim 10 wherein the antigen-specific treatment regimen comprises administering a protein, a peptide, or DNA encoding the protein or peptide.

18. The method of claim 10, wherein the autoantigens are selected from the group consisting of type II collagen; hnRNP; A2/RA33; Sa; filaggrin; keratin; citrulline; cartilage proteins; gp39; collagens type I, III, TV, V, IX, XI; HSP-65/60; IgM (rheumatoid factor); RNA polymerase; cardiolipin; aldolase A; citrulline-modified filaggrin and fibrin.

* * * * *

UNITED STATES PATENT AND TRADEMARK OFFICE
CERTIFICATE OF CORRECTION

PATENT NO. : 7,785,819 B2
APPLICATION NO. : 10/120578
DATED : August 31, 2010
INVENTOR(S) : Robinson et al.

It is certified that error appears in the above-identified patent and that said Letters Patent is hereby corrected as shown below:

In the Specification:

At Column 1, line 4 please insert the following paragraph:

--This invention was made with Government support under contract NS018235 awarded by the National Institutes of Health. The Government has certain rights in this invention.--

Signed and Sealed this

Sixteenth Day of November, 2010

David J. Kappos
*Director of the United States Patent and Trademark Office*